United States Patent
Sundrehagen

(10) Patent No.: US 9,244,063 B2
(45) Date of Patent: Jan. 26, 2016

(54) IMMUNOASSAY FOR ASSESSING RELATED ANALYTES OF DIFFERENT ORIGIN

(75) Inventor: Bärd Sundrehagen, Moss (NO)

(73) Assignee: Gentian AS, Moss (NO)

( * ) Notice: Subject to any disclaimer, the term of this patent is extended or adjusted under 35 U.S.C. 154(b) by 605 days.

(21) Appl. No.: 13/508,455

(22) PCT Filed: Nov. 11, 2010

(86) PCT No.: PCT/EP2010/067263
§ 371 (c)(1),
(2), (4) Date: Sep. 6, 2012

(87) PCT Pub. No.: WO2011/058087
PCT Pub. Date: May 19, 2011

(65) Prior Publication Data
US 2012/0322163 A1   Dec. 20, 2012

(30) Foreign Application Priority Data
Nov. 11, 2009 (EP) .................................. 09175706

(51) Int. Cl.
*G01N 33/53* (2006.01)

(52) U.S. Cl.
CPC ........................................ *G01N 33/53* (2013.01)

(58) Field of Classification Search
None
See application file for complete search history.

(56) References Cited

U.S. PATENT DOCUMENTS 6,143,559 A   11/2000   Michael et al.

FOREIGN PATENT DOCUMENTS

WO   9005144 A1   5/1990

OTHER PUBLICATIONS

Form PCT/ISA/210, WO, Feb. 10, 2011, ISR for PCT/EP2010/067263.
Form PCT/IPEA/409, WO, Jan. 31, 2012, IPRP for PCT/EP2010/067263.
Jacobsen et al: "Evaluation of a commercially available human serum amyloid A (SAA) turbidometric immunoassay for determination of equine SAA concentrations", Veterinary Journal, vol. 172, No. 2, Sep. 1, 2006, pp. 315-319, XP005587726.
Jacobsen S et al: "Evaluation of a commerically available apparatus for measuring the acute phase protein serum amyloid A in horses", Veterinary Record, vol. 163, No. 11 Sep. 13, 2008, pp. 327-330, XP009143328.
Hodek P et al: "Chicken Antibodies: Superior Alternative for Conventional Immunoglobulins", Proceedings of the Indian National Science Academy. Part Biological Sciences, vol. 69, No. 4, Aug. 1, 2003, pp. 461-468, XP009057560.
Stiborova M et al: "Sudan I is a potential carcinogen for humans: Evidence for its metabolic activation and detoxication by human recombinant cytochrome P450 1A1 and liver microsomes", Cancer Research, vol. 62, No. 20, Oct. 15, 2002, pp. 5678-5684, XP002618175.
Wehner A et al: "Utility of serum cystatin C as a clinical measure of renal function in dogs"Journal of the American Animal Hospital Association, vol. 44, No. 3, May 1, 2008, pp. 131-138, XP009143628.
Tsen YC et al: "Evauaton and vadaton of a duck IgY antbody-based immunoassay for high-sensitivity C-reactve protein: Avian antibody application in clinical diagnostics", Clinical Chemistry, vol. 49, No. 5, May 1, 2003, pp. 810-813, XP002434636.
Hansson Lo et al: "Comparison between chicken and rabbit antibody based particle enhanced cystatin C reagents for immunoturbidimetry", Jan. 1, 2008, Journal of Immunoassay and Immunochemistry, pp. 1-9, XP008093538.
Blirup-Jensen S et al.: "Protein standardization IV: Value transfer procedure for the assignment of serum protein values from a reference preparation to a target material", Clinical Chemistry and Laboratory Medicine, vol. 39, No. 11, Nov. 1, 2001, pp. 1110-1122, XP009143373.
Blirup-Jensen S et al: "Protein standardization V: value transfer. A pactical protocol for the assignment of serum protein values from a Reference Material to a Target Material", Clinical Chemistry and Laboratory Medicine, vol. 46, No. 10, Oct. 2008, pp. 1470-1479, XP002678176.
Blirup-Jensen S: "Protein standardizaiton II: Dry mass determination procedure for the determination of the dry mass of a pure protein preparation". Clinical Chemistry and Laboratory Medicine, Walter De Gruyter & Co., Berlin, New York, vol. 39, No. 11, Nov. 1, 2001, pp. 1090-1097, XP009143372, ISSN: 1434-6621.
Jonkisz et al., Acta Veterinaria Hungaria 2010, 58(1), 59-67.
Gassman et al., Faseb J. 4, 2528, 2532, 1990.
Bergstrom et al., Scandinavian Journal of Clinical and Laboratory Investigation 1980, 40(7), 637-640.
Ylng et al., Immunology 1992, 76(2), 324-330.
Greunke et al., J. Biotechnol. 2006, 124(2), 446-56.
Kohler et al., Nature 1975, 256, 495-497.
Ward et al., Nature 1989, 341, 544-546.
Bird et al., Science 1988, 242, 423-426.
Huston et al., Proc. Natl. Acad. Sci. USA 1988, 85, 5879-5883.
Holliger, P., et al., Proc. Natl. Acad. Sci. USA 1993, 90, 6444-6448.
Poljak, R.J., et al., Structur 1994, 2, 1121-1123.
Good Biotech: "CRPex-HS", May 1, 2005, p. 1 XP007916838, the whole document.

*Primary Examiner* — Gary W Counts
(74) *Attorney, Agent, or Firm* — Saul Ewing LLP; Peter C. Lauro, Esq.

(57) ABSTRACT

The disclosure describes immunoassay methods for measurements of concentrations of related analytes in samples of body fluids from different mammalian species. More particularly, the disclosure describes reagents and methods that may be used for assays of a mammalian antigen across a range of different mammalian species, using immunological reagents based on non-mammalian antibodies the mammalian antigen. In addition, a calibrator or a set of calibrators are described that are assigned with concentration values for the antigen for each of the different mammalian species.

21 Claims, 9 Drawing Sheets

Fig. 1: Schematic illustration of value assignment

Fig. 2: Schematic illustration of Analyte 1 assessment in target material

IMMUNOASSAY FOR ASSESSING RELATED ANALYTES OF DIFFERENT ORIGIN

This application is the U.S. national phase, pursuant to 35 U.S.C. §371, of PCT international application Ser. No. PCT/EP2010/067263, filed Nov. 11, 2010, designating the United States and published in English on may 19, 2011 as publication WO 2011/058587 A1, which claims priority to European application Ser. No. 09175706.2, filed Nov. 11, 2009. The entire contents of the aforementioned patent applications are incorporated herein by this reference.

The present invention relates to immunoassay methods for assessing related analytes in samples of body fluids from different mammalian species. More particularly, it provides reagents and methods that may be used for assays of a mammalian antigen across a range of different mammalian species, using immunological reagents based on non-mammalian antibodies towards said mammalian antigen. Moreover, a calibrator or a set of calibrators is provided, assigned with concentration values for the said antigen for each of the different mammalian species. The advantage of this invention is that the analytical laboratories or veterinarians may use the same reagents and method to test a plurality of different mammalian species without having to use different immunoassay reagents for different mammalian species.

BACKGROUND OF THE INVENTION

Most clinical chemistry assays—used both in human and veterinary clinical chemistry testing—measure ions, low molecule weight substances, enzymes, proteins etc. Most of these tests have been developed for human sample materials, but are also used to assay samples in veterinary medicine. Ions like sodium ions, potassium ions, manganese ions and chloride ions have identical structures in all species, and the same assay reagents may be used for determination of their concentration in samples of body liquids, cells and tissues from all species. This is also the case with small molecule substances like glucose, urea and creatinine, and most of the drugs administered to human or non-human mammals.

Enzymes from different mammalian species may have different structure, but most often they catalyse reactions of small molecule (substrates) which have identical structure in different mammalian species, and therefore the same reagents may be used to measure the enzyme activity of a class of enzymes in different mammalian species. For instance the enzyme lactate dehydrogenase may have different structure in different mammalian species, but catalyses the metabolism of lactate which has the same structure in all mammals, and the same reagents may therefore be used to measure lactate dehydrogenase enzyme's activities in samples from all mammals.

Larger molecules like proteins of different mammalian species most often differ in structure, although having the same biological function in said different species. Their concentration in samples of body liquids, cells or tissues of a species may be determined by the use of immunoassay methods, using antibodies raised in a different species by immunizing said different species with the antigen to be measured. By way of example, the concentration of human transferrin in human blood samples is often measured by using antibodies against human transferrin. These antibodies are usually made by immunizing another mammalian species (like goats, sheep, rabbits, rats or mice) with human transferrin, who recognises the human transferrin molecules as "foreign" and therefore produces antibodies towards human transferrin. There is an extensive literature on such antibody formation and immunoassay methods, e.g. "The Immunoassay Handbook" third edition by David Wild, Elsevier, Amsterdam, The Netherlands, ISBN 0 08 044 5268.

All immunoassays require standardisation. To obtain standardisation, a reference material is needed, which is used as the so-called "primary calibrator" for immunoassay measurements of an analyte. This is well-described practice (see chapter 9 of "Standardisation and Calibration" in "The Immunoassay Handbook"). Typically, the primary calibrators for protein immunoassays are based on the determination of a dry mass of a pure protein, as described by Søren Blirup Jensen in "Protein Standardization II: Dry Mass Determination procedure for the Determination of the Dry Mass of a Pure Protein Preparation" in Clin. Chem. Lab. Med. 2001; 39 (11): 1090-1097. Primary calibrators (also designated reference materials) can be made according to Blirup Jensen's protocol, or be purchased from specialised institutes like from the Institute for Reference Materials and Measurements, European Commission, Joint Research Centre. These specialised institutes provide ampoules of reference material for primary calibration of measurement systems.

"Secondary calibrators", often also called "secondary standards" are often prepared in practice in view of the very limited availability of said primary standards or calibrators. In said "Immunoassay Handbook" the preparation of secondary calibrators (or secondary standards) from a target material is described. For this purpose, a calibration curve of the signals obtained from an immunoassay system using several dilutions of the primary calibrator is prepared, and then the secondary calibrators are measured. From these results an analyte concentration value is assigned to the secondary calibrator. A detailed protocol for development of secondary calibrators is found in Blirup Jensen et al. "Protein Standardization IV: Value Transfer Procedure for Assignment of Serum Protein Values from a Reference Preparation to a Target Material", Clin. Chem. Lab. Med. 2001; 39 (11):1110-1122.

As described above, primary calibrators are used to assign analytical values to secondary calibrator materials. Immunoassay reagent manufacturers often make a secondary calibrator (with values assigned by using a primary calibrator), and store said secondary calibrator for internal use, and then use said secondary calibrator to assign values to routine calibrators which they sell to their customers. The latter calibrators could then be called a third generation calibrator, which could then be used to assign values to a fourth generation of calibrators, etc. Although proteins like albumin, transferrin, haptoglobin, haemoglobin and C-reactive protein (CRP) typically show structural and functional similarities between the different mammalian species they may be distinguished on the protein level. For example, human CRP differs from rabbit CRP on the protein level although there are many other similarities as well. Therefore, if a rabbit is immunised with human CRP, it forms antibodies towards human CRP. Dako AS, Denmark, and numerous other companies all over the world are selling such rabbit anti human CRP antibodies. However, these antibodies are not reactive to rabbit CRP (because the antibodies have been raised in rabbits), and cannot be used for immunoassays of rabbit CRP. Dependant on the actual degree of immunological similarity between the different species, said rabbit anti-human CRP antibodies may be used to measure dog CRP or goat CRP but the reaction is unpredictable, and probably significantly weaker, since all said species are mammals.

For example, rabbit anti human CRP antibodies (Dako product number Q 0329) are stated to be used for samples of human serum and plasma, samples from no other mammalian species are, however, suggested.

Other companies sell goat or sheep anti human CRP antibodies, raised in goat or sheep. These reagents cannot be used to measure goat or sheep CRP, respectively, and whether or to what extent they may be used in other mammalian species, is unpredictable. Most immunoassays used in veterinary medicine are therefore species-specific.

Dog CRP turbidimetric assays as those manufactured by TRID-Delta Company, Dublin, Ireland may be used for dog samples only.

Since many antigens have close structural relationships between different mammalian species, antibodies raised in one mammalian species against the antigen isolated from a second mammalian species may also cross-react with the same antigen from a third mammalian species. In the article "Evaluation of a commercially available human serum amyloid A (SAA) turbidimetric immunoassay for determination of equine SAA concentrations" by S. Jacobsen et al. in The Veterinary Journal 172 (2006) 315-319, the authors demonstrate that a commercial assay used (based on rabbit antibodies towards human SAA) could be used to determine SAA concentrations in body liquid samples from horses. However, no real assay was described, merely relative responses of different horse SAA were measured. Moreover, the system was calibrated with human SAA calibrator solutions.

Jonkisz et al report in Acta Veterinaria Hungarica (2010) 58(1), 59-67 on a comparison of turbidimetric and nephelometric assay results for Cystatin C in dogs. Both assay formats (PETIA and PENIA) were based on the use of rabbit anti-human Cystatin C antibodies, i.e. both assays were calibrated with human Cystatin C. No correlation between said two assay methods if applied to dog Cystatin C was observed, as illustrated by a correlation coefficient of merely 0.706 and it is suggested to consider carefully future validation procedures of PETIA and PENIA in the dog. Actually said results indicate that assays calibrated for an analyte of a different species are unreliable, most probably due to the completely unpredictable levels of cross-reactivity of the human anti Cystatin C antibodies with dog Cystatin C. Nevertheless, the authors of said paper did not consider an approach based on a calibration of these assay with dog Cystatin C.

In "The Veterinary Record" Sep. 13, 2008, 163, 327-330, Jacobsen et al. described in their article "Evaluation of a commercially available apparatus for measuring the acute phase protein Serum Amyloid A in horses" another immunoassay system where rabbit antibodies towards human SAA were used to determine the SAA concentration in body liquid samples from horses. In FIGS. 3 and 4 of said article, the authors point to the differences in calibration between the two systems and do not point to any attempt to validate the reported horse SAA protein concentrations in the samples analysed.

In *Clinical Chemistry* 49, No. 5, 2003, p. 810-813, Tsen et al. report in the article "Evaluation and Validation of a duck IgY Antibody based Immunoassay for High-Sensitivity C-reactive Protein: Avian Antibody Application in Clinical Diagnostics" on a duck IgY turbidimetric CRP measurement product from Good Biotech Corporation in Taiwan. This is the only known turbidimetric CRP assay using avian non-mammalian antibodies. At the end of said report the advantages of the use of avian antibodies in diagnostic human medicine are discussed. There is no hint whatsoever that these reagents have any universal use among all mammalian species.

In the article "Comparison between Chicken and Rabbit Antibody Based Particle Enhanced Cystatin C Reagents for Immunoturbidimetry" in Journal of Immunoassay & Immunochemistry, 29: 1-9, 2008, L.-O. Hansson et al. report on the advantages of the use of avian IgY antibodies (compared to mammalian antibodies) in particle enhanced immunoturbidimetric methods, which again only discuss the advantages for measurements of human samples. There is no hint to the advantage of using such antibody-based particles across the species boundaries among mammals.

Gassman et al. report in Faseb J. 4: 2528, 2532, 1990, the efficient production of chicken egg yolk antibodies against a conserved mammalian protein.

In Proc. Indian Natn Sci Acad. B69 No. 4 pp 461-468 (2003), in the article "Chicken Antibodies—Superior Alternative for Conventional Immunoglobulins", Hodek and Stiborova mention that avian antibodies react with many epitopes due to the genetic differences between avians and mammals, and cause less interference in studies of human samples. Avian antibodies against rat CYP1A1 (a P450 enzyme) also react with human CYP1A1 at a very low detection limit. Hodek and Stiborova, however, do not raise the issue of calibration of the immunoassay response when cross-reactivity occurs. They also teach away from using turbidimetric methods using IgY, since they state that "the only limitation of chicken antibody application consists in the lower ability of IgY to precipitate antigens." They do not propose the use of particle enhancement of the signal; instead they propose "however, using optimized reaction conditions, formation of precipitate can be facilitated (e.g. by using a higher ionic strength)". Moreover, there is no mentioning of using calibrators with antigens from another mammalian species. They use preparations of human CYP1A1 when they test for human CYP1A1, and rat CYP1A1 when they test for rat CYP1A1.

In general, polyclonal antibodies are preferred over monoclonal antibodies in turbidimetric assays, since polyclonal antibodies solutions generally react with more epitopes on the antigens to be detected. The article "An automated turbidimetric immunoassay for plasma proteins" Bergström and Lefvert in Scandinavian Journal of Clinical and Laboratory Investigation, Vol. 40, 7, November 1980, 637-640, is one of many examples on how polyclonal antibodies are preferred over monoclonals in turbidimetric measurements. However, cocktails of monoclonals—or simply one monoclonal if the antigen is a polymer or consists of more than one subunit with the same epitopes—may be used, like in the Roche Diagnostics Tinaquant CRP assay.

In Immunology, 1992, 76(2): 324-330, Ying et al. report in the article "Reactivity of anti-human C-reactive protein (CRP) and serum amyloid P component (SAP) monoclonal antibodies with limulin and pentraxins of other species" that monoclonals to human serum proteins like CRP and Serum Amyloid A also may react towards said proteins from other mammalian species. The article indicates that this may occur or not, and cannot be generally relied upon. It is totally dependant on whether the epitope on the antigen—against which the monoclonal antibody is directed—is present in an unaltered structure in the different mammalian species.

Avian monoclonal antibodies exist, however, they have not come into use yet. Examples on such literature may be found in J. Biotechnol. 2006 Jul. 13; 124(2):446-56, with the title "Bivalent monoclonal IgY antibody formats by conversion of recombinant antibody fragments", and in U.S. Pat. No. 6,143, 559—"Methods for the production of chicken monoclonal antibodies" by Michael et al.

SUMMARY OF THE INVENTION

It is an object of the present invention to provide a novel immunological assay format, applicable in human or in particular veterinarian medicine, which allows the assessment of a multiplicity of related analytes derived from different sources with a minimum number of immunological reagents.

Said problem was surprisingly solved by providing the immunological assay method and calibrator compositions as set forth in the attached claims and explained in more detail below.

As explained in more detail below the advantages over the prior art are that in the assays of the present invention, only one secondary calibrator material or a set of dilutions of secondary calibrator material is needed to assay, for example, body liquid samples from several mammalian species, for the same (antigenically related) analyte.

DEFINITIONS OF GENERAL TERMS

Figure 1:
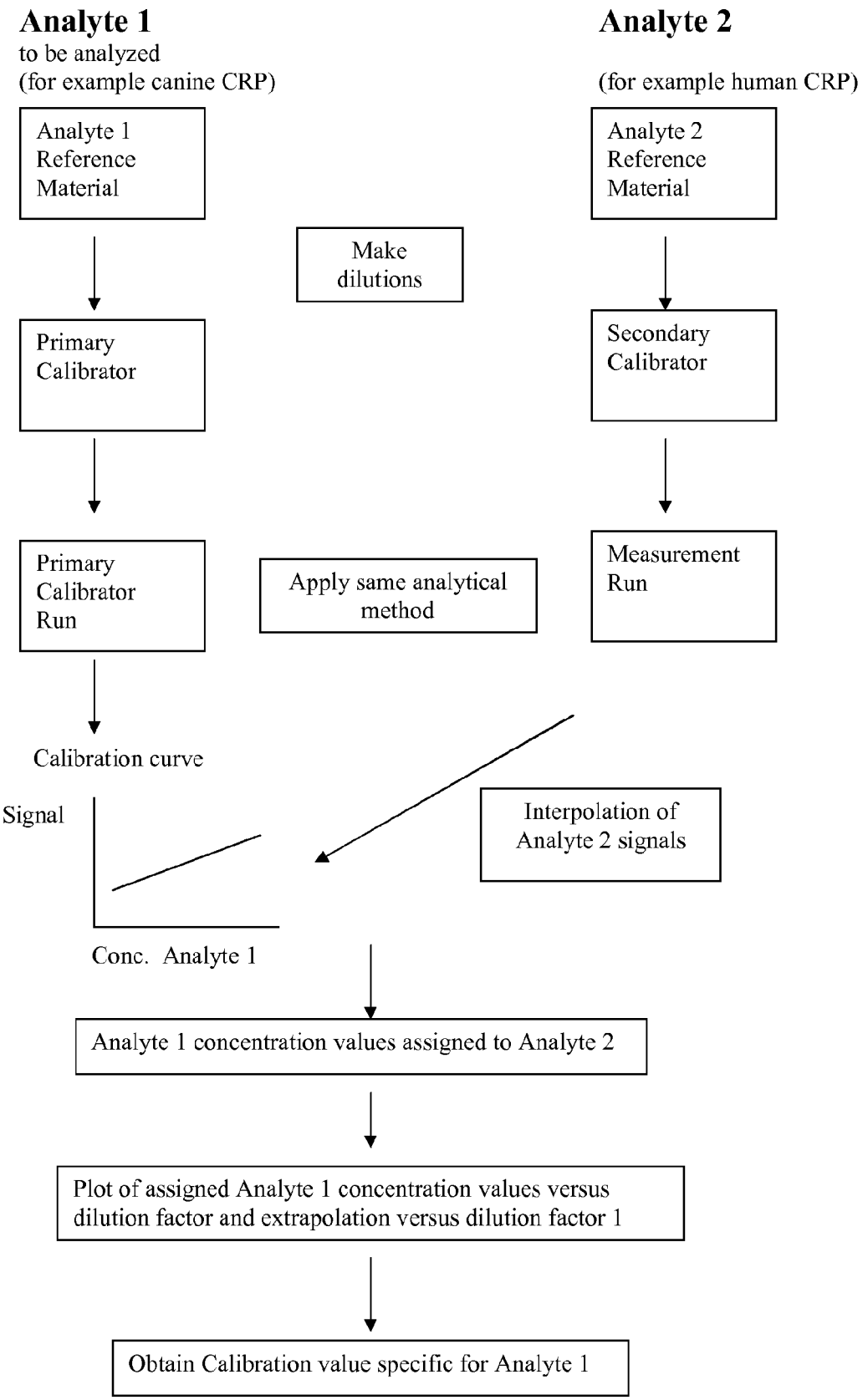
FIG. 1 illustrates schematically an embodiment of the invention, which may be applied in order to assign a calibration value specific for a primary calibrator (Analyte 1, for example canine CRP) to a secondary calibrator (Analyte 2, for example human CRP).

"Biological activity" as used herein, refers to any inherent biological properties of an analyte as defined herein.

The term "secondary calibrator" is used for all calibration materials having been assigned values using a primary calibrator, whether the secondary calibrator has been assigned with a value using a primary calibrator directly, or whether it is derived via other calibrators, where said other calibrators have been assigned values using a primary calibrator or any reference material. The secondary calibrator comprises a substance (Analyte 2), as for example a protein, related to the substance to be finally assessed (Analyte 1) as herein defined in more detail. Said substance may be contained in any, in particular liquid, phase, like water or buffer solution. However it may also be contained in a medium resembling to liquid medium to the analyte finally to be assessed. For example, if a blood serum sample has to be analysed for Analyte 1 it may be of advantage if the corresponding Analyte 2 of the secondary calibrator is provided in normal blood serum (optionally processed by centrifugation in order to remove insoluble constituents).

The term "primary calibrator" as used herein may be based on the determination of a dry mass of a pure protein to be analysed (Analyte 1), as described by Søren Blirup Jensen in "Protein Standardization II: Dry Mass Determination procedure for the Determination of the Dry Mass of a Pure Protein Preparation" in Clin. Chem. Lab. Med. 2001; 39 (11): 1090-1097. Primary calibrators can be made according to Blirup Jensen's protocol, or be purchased from specialised institutes like from the Institute for Reference Materials and Measurements, European Commission, Joint Research Centre. In addition the term "primary calibrator" as used herein also encompasses any other suitable reference material allowing calibrating for a protein to be analysed (analyte 1). As for example said material may be derived from a natural source containing, in admixture with further constituents" said desired protein at specified—often but not always—at elevated concentrations. As exemplified later, for example, horse serum with high CRP values may be used as "primary calibrator" instead of pure house CRP per se. In other assay situation, e.g. for assays of bovine transferrin, bovine serum-based calibrators with specified and different concentrations of bovine transferrin covering the normal reference range of transferrin in bovine animals, and often one calibrator above the reference concentration range and one calibrator below the reference range, dependant on the assay measurement range intended.

A "target material" refers to a sample to be analysed for the presence of an analyte. Typically said target material represents a more or less complex natural or artificial mixture of chemical and/or biochemical substances. Organic and/or inorganic high- and/or low-molecular substances may be present at the same time in solid, dissolved or dispersed form.

A "body liquid sample" as used in the assay method according to the invention is a sample derived from an organism, in particular a mammal species, which contains an analyte to be assessed. Any analyte containing liquid sample may be used. Said samples to be assayed according to the invention may be any analyte containing biological fluid or tissue extract and may be pre-treated prior to the assay. Examples of suitable samples are blood, blood fractions, like serum and plasma, and pre-treated blood, like EDTA-blood, or EDTA-plasma, citrate-plasma, heparin plasma, or urine samples. The originally obtained samples or fractions thereof may be further modified by methods known in the art, as for example by fractionation or dilution. Fractionation may be performed to remove constituents, which might disturb the assay. Dilution may be performed by mixing the original sample or a fraction thereof with a suitable sample liquid, like a suitable buffer, in order to adjust the concentration the constituents, as for example of the analyte. Such modified samples exemplify samples "derived from" the original body fluid sample "collected" or "isolated" from the organism like a mammal.

An "analyte" to be assayed according to the invention is any antigenic substance as formed by or observed in an organism like the body of a healthy or diseased mammal. Although not necessary, it may also be possible to use as the analyte a derivative of said analyte or a mixture of the natural analyte and analyte derivative(s). Non-limiting examples of analyte derivatives are analyte compounds carrying a suitable detectable marker, as for example a radioactive metal or chromophor label.

An analyte "wholly or partly derived" from an organism means that said analyte is either assessed in the form occurring in the target material or body liquid sample to be analyzed (i.e. the analyte is "wholly derived"), or is assessed after having been modified or derivatized as explained above (i.e. the analyte is partly derived).

"Assessing" or "assessment" is intended to include both quantitative and qualitative determination in the sense of obtaining an absolute value for the amount or concentration of the analyte present in the sample, and also obtaining an index, ratio, percentage, visual or other value indicative of the level of analyte in the sample. Assessment may be direct or indirect and the chemical or biochemical species actually detected need not of course be the analyte itself but may, for example, be a derivative thereof.

An "analytical value" refers to the result of the assessment of the analytical method and may be a proportion or concentration value of the analyte in the target material.

An "analytical signal" may be any chemical, biological or physical, in particular optical, generated by an analytical method or apparatus which my serve as a qualitative or quantitative indicator of an analyte to be analyzed by said method. For example said signal may be change in the intensity of light of a specific wavelength.

"Homogeneous immunoassays" are, as opposed to "non-homogeneous immunoassays", simpler in construction and have a higher throughput capacity. In particular, homogeneous assays do not encompass a pre-treatment step of the sample in the form of separation step, for example by applying the sample on a solid matrix, like a chromatography column, and separating the analyte from parts of the original constituents of the original complex sample. For a homogeneous assay the sample and reagents are mixed, incubated and measured, either during or after incubation. Endpoint signals or differences in signal between different time points or continuous kinetic measurements are used. Both assay formats are encompassed by the invention.

"Particle enhanced" measurements or immunoassays are based on the "light scattering properties" associated with the nanoparticles or nanoparticle-immunoconjugates. Such nanoparticles are usually approximately spherical, preferably with a narrow size distribution. The size of said particles is normally expressed via their mean diameter. According to the well-known laws of light scattering said light scattering properties may be influenced by the particle size, and/or the ratio of the refractive index of the particle to that of the medium. Weak light scattering properties may result from a small particle size, and/or a low ratio of the refractive index of the particle to that of the medium (see also Rayleigh's law of light scattering). Examples of such "particle enhanced" assays are turbidimetric (PETIA) or nephelometric (PENIA) immunoassays.

The size and/or the refractive index ratio of the nanoparticles are such that they can cause light scattering at the wavelength used for detection of agglutinated nanoparticle-immunoconjugates. That size is generally chosen to be smaller than that detection wavelength.

The "detection wavelength" refers to the wavelength of light for measuring the change of turbidity, for example by measurement of light absorption or by measuring light scattering, in the sample. Usually it may be in the range of from 300 nm to 1200 nm, like from 400 to 700 nm or from 500 to 600 nm. Optimum detection wavelength values may be chosen by s skilled person. For example in order to increase assay sensitivity a lower wavelength may be of advantage. Increasing the assay capacity may require a higher wavelength to be selected.

The "accuracy" of an analytical method of the present invention, is the methods ability to accurately determine the concentration of the analyte in a sample, compared to the concentration as determined by an even more reliable reference method.

The "precision" of an analytical method of the present invention, is the variation in the results when the concentration of the analyte in a sample is determined repeatedly.

A "robustness" of an assay according to the present invention is the methods ability to tolerate interfering substances and variations in assay conditions without influencing the resulting analytical concentration value determined for the analyte.

An "inert protein" as used in the context of the invention is a protein of any origin (for example, human or non-human mammalian, microbial) which does not disturb the assay method of the invention; in particular it should have substantially no or no detectable affinity for the analyte to be assessed and/or for the antibodies as used in the assay method of the invention.

In a "competitive immunoassay", the antigen in the unknown sample competes with labeled antigen to bind with antibodies. The amount of labeled antigen bound to the antibody site is then measured. In this method, the response will be inversely proportional to the concentration of antigen in the unknown. This is because the greater the response, the less antigen in the unknown was available to compete with the labeled antigen Most immunoassay methods today run on auto-analyzers having auto-dilution to obtain calibrator curves with different concentrations of the antigen. However—also many end users prefer to obtain sets of calibrators being diluted to the preferred concentrations by the supplier of the reagents. When the language "one calibrator material" is used in the description of the present invention, it may be in the form of one single vial (to be diluted at the time of use), or a single set of calibrator solutions being diluted by the supplier.

"Antigenically related" or "immunological related" are compounds, each of which being recognized by the same immunological reagent or antibody preparation (for example monoclonal antibody) otherwise however distinguishable either with respect to the binding characteristics of said immunological reagent or antibody preparation (for example by showing different binding kinetics), or distinguishable by the additional binding an immunological reagent or antibody preparation of different antigen binding specificity. Thus antigenically related compounds either share at least one common antigenic determinant, being of sufficient similarity to be recognized by the same immunological reagent or antibody preparation; or share at least one common identical determinant and at least one determinant specific for each of said compounds based on which said compounds might be further differentiated.

Particular examples of such "antigenically related" or "immunological related" compounds are homologues or variants of a biological compound, for example a protein or enzyme, to be assessed. Such variants may differ on the level of amino acid sequence and may be defined by a degree of sequence identity which is less than 100%, as for example 10 to 99.9% or 20 to 90% or 50 to 80% meaning the percentage identity of the amino acid residues relative to the total length of one specific the amino acid sequences of said variants. Said variant may be specific for a particular mammalian species of a particular physiological or disease state of a mammalian species. Said variant may be naturally occurring or be the result of genetic mutation.

"Functionally related" refers to compounds, here in particular analytes to be assayed, which concur in at least one biological activity. Said biological activities will, however, be quantitatively different. For example, the analyte may show an enzyme activity characterized by conversion of at least one substrate molecule to the same product, however with different conversion rate and or yield. "Functionally identical" compounds on the other hand refer to those compounds, which show at least one quantitatively identical biological activity.

"Antibody" or "immunological reagent" designate, unless otherwise stated the same type of molecule, said molecule being characterized by binding an antigen or a number of antigenically related antigens.

The term "antibody", as used herein, broadly refers to any immunoglobulin (Ig) molecule, mostly comprised of four polypeptide chains, two heavy (H) chains and two light (L) chains, or any multimer, functional fragment, mutant, variant, or derivation thereof, which retains the essential epitope binding features of an Ig molecule. Such mutant, variant, or derivative antibody formats are known in the art.

Immunoglobulin molecules can be of any type (e.g., IgG, IgE, IgM, IgD, IgA and IgY), class (e.g., IgG 1, IgG2, IgG 3, IgG 4, IgA1 and IgA2) or subclass.

An antibody is said to be "capable of binding" a molecule if it is capable of specifically or non-specifically reacting with the molecule to thereby bind the molecule to the antibody.

A "monoclonal antibody" as used herein is intended to refer to a preparation of antibody molecules, which share a common heavy chain and common light chain amino acid sequence, in contrast with "polyclonal" antibody preparations that contain a mixture of different antibodies. Monoclonal antibodies can be generated by several novel technologies like phage, bacteria, yeast or ribosomal display, as well as classical methods exemplified by hybridoma-derived antibodies (e.g., an antibody secreted by a hybridoma prepared by hybridoma technology, such as the standard Kohler and Milstein hybridoma methodology ((1975) Nature 256:495-497).

In a full-length antibody, each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4.

The term "antigen-binding portion" or "antigen-binding fragment" of an antibody (or simply "antibody portion" or "antibody fragment"), as used herein, refers to one or more fragments of an antibody that retain the ability to specifically bind to an antigen. It has been shown that the antigen-binding function of an antibody can be performed by fragments of a full-length antibody. Such antibody embodiments may also be bispecific, dual specific, or multi-specific formats; specifically binding to two or more different antigens.

Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546, Winter et al., PCT publication WO 90/05144 A1), which comprises a single variable domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., et al. (1994) *Structure* 2:1121-1123). Such antibody binding portions are known in the art (Kontermann and Dubel eds., *Antibody Engineering* (2001) Springer-Verlag. New York. 790 pp. (ISBN 3-540-41354-5).

Particular Embodiments of the invention:

The present invention relates to the following particular embodiments:

1. An immunological assay method for assessing at least one first analyte suspected to be contained in a target material of or obtained from at least one first organism or being of at least one first origin, in particular animal species like non-mammalian or, in particular, mammalian species, which method comprises
   a) obtaining a first analytical signal for said first analyte, and
   b) assessing said first analyte by correlating said first analytical signal for said first analyte with a second analytical signal obtained for a second analyte, which also may be designated reference or calibrator analyte of a second organism or being of a second origin, in particular animal species, like non-mammalian or, in particular, mammalian species different from the first, said second analyte being immunologically related to the first analyte; wherein said first and second analytical signal are obtained with the same, i.e. identical, immunological reagent, in particular under substantially identical assay conditions, as for example same, i.e. identical, analytical apparatus, same, i.e. identical, or comparable constituents of assay mixture, like biological constituents.

2. The assay method of embodiment 1, wherein said first and said second analytical signal are obtained be the same, i.e. identical, analytical method using the same, i.e. identical, antibody preparation.

3. The assay method of one of the preceding embodiments, wherein said first and second organism are different animal species.

4. The assay method of one of the preceding embodiments, wherein said first and second analyte are functionally related (i.e. having a similar physiological or pathological, biological or chemical function in an organism) and antigenically related, so that they may be recognized by the same antibody.

5. The assay method of one of the preceding embodiments, wherein said first and second analyte are functionally substantially identical (i.e. having substantially identical physiological or pathological, biological or chemical function in an organism) and antigenically related.

6. The assay method of one of the preceding embodiments, wherein said first and second analyte are antigenically related and recognized by the same immunological reagent (or binding molecule) (like monoclonal antibody or polyclonal antibody preparation).
7. The assay method of embodiment 6, wherein said immunological reagent (or binding molecule) is generated by means of an immunological procedure, comprising classical immunization procedures in order to generate said reagent and screening methods, based on suitable libraries of binding molecules, making use of the second analyte as antigen.
8. The assay method of embodiment 7, wherein said immunological procedure is based on (i.e. makes use of) a third organism different from the first and second organism, i.e. wherein said third organism is immunized with said antigen and a binding protein library derived from said third organism is applied for screening for suitable binding protein candidates.
9. The assay method of one of the preceding embodiments, wherein said first and second organism are different mammalian species, wherein said mammalian species may, for example, be selected from man, dog, horse, cow, pig, cat, rabbit.
10. The assay method on one of the embodiments 8 and 9, wherein said third organism is selected from a non-mammalian species.
11. The assay method of embodiment 10, wherein said non-mammalian species is avian, as for example chicken or duck.
12. The assay method of one of the preceding embodiments, which is a particle-based immunological method.
13. The assay method of embodiment 12, which is a turbidimetric or nephelometric method.
14. The assay method of embodiment 13, wherein said method comprises applying a nanoparticle-antibody conjugate comprising nanoparticles suitable for turbidimetric or nephelometric measurement, where said nanoparticles are coated with an immunological reactant as defined in anyone of the embodiments 6 to 11.
15. The assay method of embodiment 14, wherein the nanoparticles are coated with polyclonal avian antibodies or antigen binding fragments thereof, reactive with said first and second analyte.
16. The assay method of one of the preceding embodiments, wherein a body liquid sample of a first mammalian species is analyzed as target material suspected to contain the first analyte (also designated herein "analyte 1").
17. The assay method of one of the preceding embodiments, wherein the first analyte is selected from a biological marker associated with a dysfunction, disease or clinical condition of said first organism or a condition accompanying the same.
18. The assay method of embodiment 17, wherein said marker is selected from macromolecules, in particular proteins, like enzymes, polypeptides, cell surface proteins), glycoproteins, proteoglycanes, nucleic acids, and fragments derived there from.
19. The assay method of embodiment 18, wherein said marker is selected from CRPs, transferrins, albumins, serum amyloid protein A, calprotectin, haptoglobin, choriongonadotropins, thyroid stimulating hormone, ferritin, different immunoglobulin classes, insulin, and prostate specific antigen.
20. The assay method of one of the preceding embodiments wherein a multiplicity of first analytes from a multiplicity of first organisms is assessed (or assessable) by correlating a multiplicity of first analytical signals for said multiplicity first analytes with a second analytical signal obtained for one (single) second reference analyte (also designated herein "analyte 2") of a second organism, in particular animal, more particular mammalian species,) different from said multiplicity of first organisms, in particular animals, more particular mammalian species.
21. The assay method of anyone of the preceding embodiments, which is a turbidimetric assay for assessing a first antigenic substance (i.e. first analyte) in a body liquid sample from a first mammalian species by
   a) forming an assay mixture by contacting said sample with a nanoparticle antibody conjugate comprising nanoparticles suitable for turbidimetric measurement, where said nanoparticles are coated with monoclonal or in particular polyclonal non-mammalian, in particular avian antibodies or binding fragments thereof reactive with said first antigenic substance from said first mammalian species, and
   b) assessing the content of said first antigenic substance by measuring the change in turbidity of said mixture,
   wherein the said monoclonal or in particular polyclonal antibodies have been raised against a second antigenic substance (i.e. second analyte) derived (i.e. obtained or isolated) from a second mammalian species different from said first mammalian species, and wherein said first and second antigenic substance are different but structurally and/or functionally, in particular immunogenically related (in particular homologues or variants thereof).
22. The assay according to embodiment 21, which is a turbidimetric method being further characterized by assessing the content of the first analyte by measuring the change in turbidity of the assay mixture and comparing the observed change in turbidity to changes observed using calibrators with known concentrations of said second analyte from second mammalian species.
23. The assay method according to one of the preceding embodiments, where the assay is calibrated by means of said second analyte or by means of a composition comprising said second analyte wholly or partially derived from said second mammalian species and different from said first mammalian species from which the said target material, suspected to contain the first analyte has been taken, wherein for said second analyte or said composition comprising said second analyte a calibration value valid for the first analyte has been assigned in a manner known per se in the field of assay calibration or, in particular, as explained in more details in the experimental part. In case a multiplicity (i.e. 2, 3, 4, 5, 6, or more; like up to 20, up to 15 or up to 10) of first analytes has to be assessed (as for example same protein or enzyme, like CRP, CysC, albumin, isolated from different organisms), a proper multiplicity of corresponding calibrator values has to be assigned.
24. The assay method of one of the preceding embodiments, wherein said second analytical signal obtained for said second analyte of said second mammal is correlated with said first analytical signal for said first analyte by assigning an analytical value, as for example a concentration value, derived from a calibration curve for said second analyte to said first analytical signal of said first analyte (see also FIG. 2).
25. The assay method of embodiment 24, wherein said assigned analytical value is further corrected by means of a calibration value as obtained for said first analyte. Obtaining a calibration value for an analyte to be assesses is further illustrated by FIG. 1.

26. A calibrator composition of assays of a first antigenic substance (or first analyte) in a target material like body liquid samples from a first organism (first mammalian species), said calibrator composition comprising a second antigenic substance wholly or partially derived from a second organism (second mammalian species) different from said first organism (first mammalian species) from which said target material (said the said body liquid sample) has been taken, but assigned with a calibration value valid for said target material or first analyte (like body liquid samples from said first organism (first mammalian species) from which said target material (or sample) has been taken.

27. A calibrator composition of embodiment 26, assigned with calibration values valid for more than one first organisms (first mammalian species) for which the first analyte is to be assessed.

28. The calibrator composition of embodiment 26 or 27, which is for calibration of CRP assays.

29. A method of obtaining a calibration value for at least one first analyte to be assessed, which method comprises the steps of:
    a) generating a calibration curve with a (standardized) primary calibrator material of a first analyte, by plotting analytical signals (like absorbances) versus related dilutions of said first analyte;
    b) obtaining corresponding analytical signals for different dilutions of a second analyte (related to said first analyte), (steps a and b being performed in any order)
    c) deriving from said calibration curve of step a) a first analyte-related parameter, like amount concentration, and assigning it to the corresponding signal of the second analyte.

30. The method of embodiment 29, further comprising plotting to assigned first-analyte-related parameters versus the corresponding dilution factors, extrapolating versus dilution factor one and obtaining a calibration value specific for the first analyte if assessed with said second analyte as (secondary) calibrator.

Embodiments 29 and 30 are further illustrated by FIG. 1. More detailed explanation of particular embodiments of the invention:

The present invention is, inter alia, based on the surprising observation that immunoturbidimetric assay reagents, for example, based on avian antibodies immobilised on nanoparticles can be made and used for immunoturbidimetric assays of antigens in body liquids from different mammalian species, even though the antigenic structure for said antigen varies in said mammalian species. By the use of immunoparticles where avian antibodies have been immobilised, not only general immunological responses could be observed, but calibrated immunoturbidimetric assays were developed where in the same assay reagents may be used for assaying concentrations of a specific antigen, as for example CRP, in body liquid samples of a multiplicity (i.e. one or more) different mammalian origin, without the need of providing specifically adapted reagents for said multiplicity of different mammalian species.

By forming an assay mixture by contacting a body liquid sample with a nanoparticle antibody conjugate comprising nanoparticles suitable for turbidimetric measurement, where said nanoparticles are coated with avian antibodies or fragments thereof reactive with said antigenic substance (like CRP) from a first mammalian species, immunoturbidimetric signals useful for quantitation of said antigen were obtained. Said immunoturbidimetric signals were obtained, whether the said polyclonal avian antibodies have been raised against the said antigenic substance (like CRP) derived from a mammalian species different from which the body liquid sample had been taken, or whether the said avian antibodies had been raised against said antigenic substance (like CRP) derived from the same mammalian species. The content of the antigenic substance (like CRP) in said body liquid was assessed by measuring the change in turbidity of said assay mixture.

A further advantage of the present invention is that—based on the described use of immunoparticles suitable for turbidimetric measurement, where said nanoparticles are coated with avian antibodies or fragments thereof reactive with said antigenic substance (like CRP) from said mammalian species—also the same calibrator substance (like CRP) could be used for calibrating assays for concentration of a related antigen in a body liquid sample from one or more different mammalian species. The calibrator composition may comprise antigen substance (like CRP) wholly or partially derived from a mammalian species different from the species from which said body liquid sample has been taken, or wholly or partly from the same mammalian species from which said body liquid sample has been taken. This is achieved by the use of the said nanoparticles that have been coated with polyclonal avian antibodies towards the antigen (like CRP) from a different mammalian species, and using an assignment protocol for setting the correct calibrator value on the calibrator material.

A particular analytical protocol involves the following steps:

Step A: A primary calibrator for an antigen (like CRP) (in pure form) from a specified first mammalian species is prepared using an independent method, e.g. by gravidimetric methods well known in the prior art. Such teaching is provided, for example, by Søren Blirup Jensen "Protein Standardization II: Dry Mass Determination Procedure for the Determination of the Dry Mass of a Pure Protein Preparation" in Clin. Chem. Lab. Med. 2001; 39 (11): 1090-1097, incorporated herein by reference.

Step B: A secondary calibrator is prepared comprising the related antigen (like CRP) from any of one or more second mammalian species (different from the first mammalian species). This secondary calibrator is assayed using the said immunoparticles suitable for turbidimetric measurement, where said nanoparticles are coated with avian antibodies or fragments thereof reactive with said antigen (like CRP), and a value is assigned for each mammalian species using the method as taught by Blirup Jensen et al. "Protein Standardization IV: Value Transfer Procedure for Assignment of Serum Protein Values from a Reference Preparation to a Target Material", Clin. Chem. Lab. Med. 2001; 39 (11):1110-1122, incorporated herein by reference.

The starting point for step A above may also be a primary calibrator comprising the antigen of the specified first mammalian species not in pure form but at specified concentration levels, often—but not always—at elevated concentration levels. The concentration levels chosen for the calibrators or the calibrator is chosen dependant on the intended assay measurement range.

Following such a protocol using the present invention, a secondary calibrator and turbidimetric assay reagents are provided which can be used for quantitation of the antigenic substance (like CRP) in body liquid samples from a multiplicity of different mammalian species. Thus, just one set of reagents and one secondary calibrator material are necessary for assaying the antigenic substance (like CRP) from one or more different mammalian species. For each specific mammalian species, a calibration value assigned to said secondary calibrator for said species is used to calculate the result of the assay for the body liquid sample of from said mammalian species. Thus, said secondary calibrator—although being the same secondary calibrator material—may have assigned different or slightly different calibration values for the use in assays of samples from different mammalian species.

CRP is an antigenic substance, which has been measured in different mammalian species using specific reagents for each mammalian species, as outlined in the background of the present invention. By following the present invention, in particular by forming an assay mixture by contacting a body liquid sample with a nanoparticle antibody conjugate comprising nanoparticles suitable for turbidimetric measurement, where said nanoparticles are coated with avian antibodies (or fragments thereof) reactive with CRP from a mammalian species, immunoturbidimetric signals useful for quantitation of CRP were obtained. Said immunoturbidimetric signals were obtained, whether said polyclonal avian antibodies have been raised against CRP substance derived from a mammalian species different from which the body liquid sample had been taken, or whether said avian antibodies had been raised against CRP derived from the same mammalian species. The content of CRP in said body liquid could be assessed by measuring the change in turbidity of said assay mixture.

Figure 2:
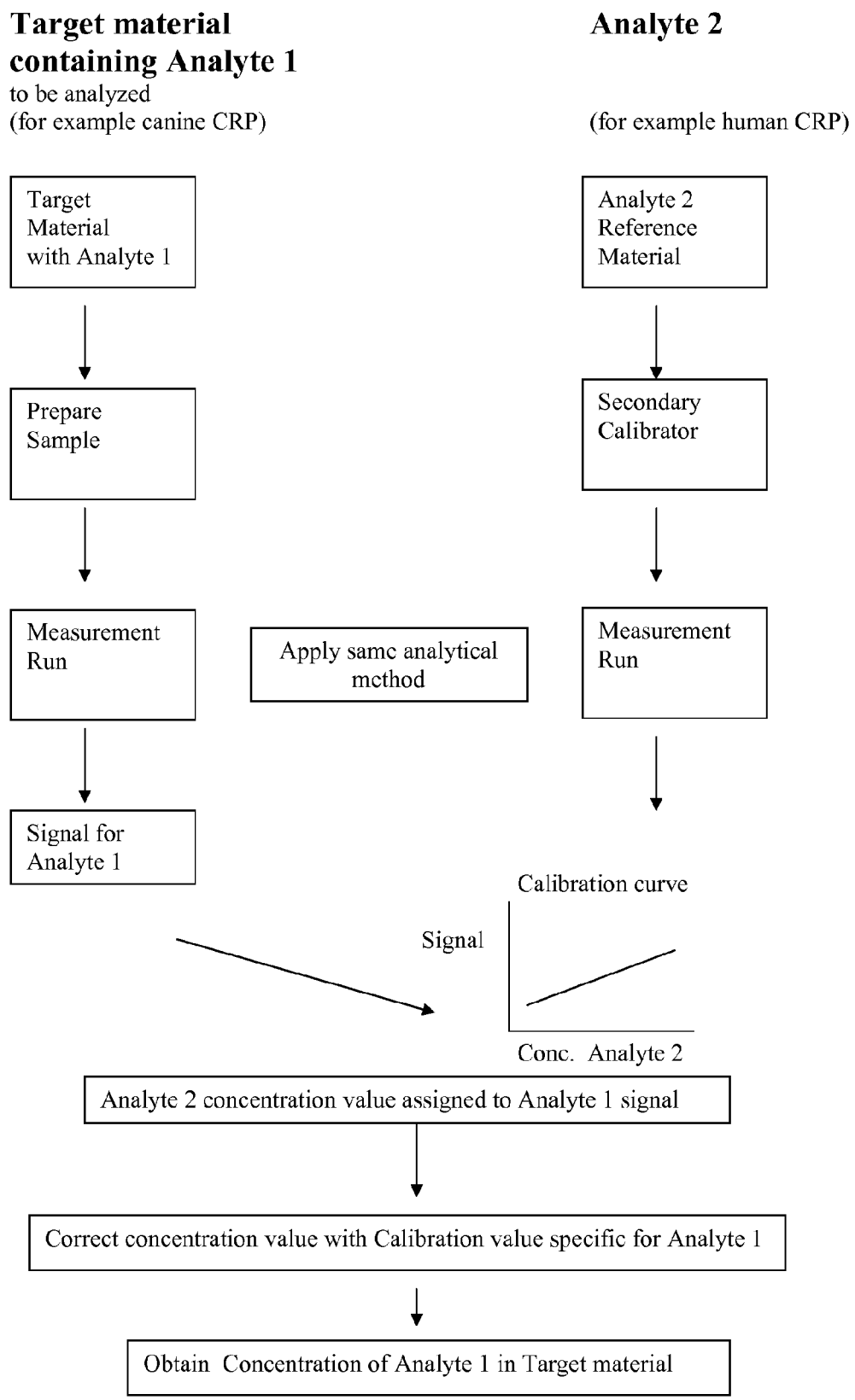
FIG. 2 illustrates schematically an embodiment of the invention which may be applied in order to assess in a target material the actual concentration of Analyte 1 (for example canine CRP) based on a calibration curve generated with, for example, human CRP as secondary calibrator (Analyte 2). Based on the analytical signal obtained for Analyte 1 and the concentration derived from the calibration curve for Analyte 2 (Analyte 2 concentration assigned to Analyte 1) the actual concentration of Analyte 1 in said target material is calculated by correcting first concentration value with the calibration value specific for Analyte 1 as obtained according to FIG. 1. If a multiplicity of calibration values (generated according to FIG. 1) is available for several different Analytes 1 (for example canine, horse, cow, pig) the same secondary calibrator (Analyte 2) may be applied in order to assess concentrations of each of said Analytes 1 in different target material.

The basic principle of value assignment and assessment of an analyte, as for example canine CRP with human CPR as secondary calibrator, is also illustrated by FIGS. 1 and 2, the disclosure of which is not intended to be limited to said specific analyte, but may be transferred to practically any other (first) analytes (s) for which corresponding second analytes (artificial or partially or fully derived from other organism or origin) exist.

Similar methods for plasma proteins like transferrin, Serum-amyloid A, pre-albumin and urine albumin are made available by the following the teaching of the present invention.

Nanoparticles of different compositions may be used for the present invention, and different conjugation methods well known in the prior art can be used. Latex nanoparticles, naked or functionalised, are obtainable from Invitrogen (US) or Merck Prolabo (France), and numerous coupling protocols are available in the literature and in technical bulletins from suppliers like Bangs Particles Inc (US). Gold colloids may be especially preferred materials, and are taught in numerous articles in the prior art, one such example being U.S. Pat. No. 5,334,538.

Nanoparticles coated with antibody binding proteins, like secondary anti-avian antibodies from goat or rabbit—may be used as well.

Most turbidimetric immunoassays employ direct non-competitive measurement principles: Antibodies towards the antigenic substance are immobilised on particles which agglutinate in the presence of antigen.

A competitive principle may also be employed: Antigens, or portions of the antigen or derivatives of the antigen or hapten or epitope of the antigen, are immobilised on the particles, which agglutinate when antibodies or immunoactive fragments or derivatives thereof are in the solution. When antigens from sample materials are present in the solution, they compete for the antibodies in the solution, and will reduce the rate or the extent to which the particles agglutinate.

All examples above are non-competitive turbidimetric assays, but the present invention is not limited to the use of non-competitive immunoassays. These assays—and other assays—can be made in a competitive way, e.g. where the nanoparticles have been made with antigens immobilized on the surface, and the nanoparticles, the sample to be tested and antibodies are added to the assay mixture. Then the antigens from the test sample compete for the antibodies with the antigens immobilized on the nanoparticles, and high content of antigens in the test sample result in lower agglutination of the particles than when low contents of the antigen are present in the sample. This is straight forward immunoassay technology well known to the skilled man of the art, and is taught in "The Immunoassay Handbook" third edition by David Wild, Elsevier, Amsterdam, The Netherlands, ISBN 0 08 044 5268, and many other reference textbooks and other publications.

Further embodiments of the invention:

1. Coated Nanoparticles:

The coated nanoparticles which may be used according to the invention may have a mean diameter of at least about 20 nm, as for example 20 to 500 nm, or 20 to 400 or 20 to 300 nm, in particular a mean diameter in the range of 25 to 220, 35 to 175, 50 to 140, 70 to 120, 75 to 110, 80 to 105, or 90 to 95 nm. They are coated with a layer of antibodies or antigen or fragments or conjugates of antibodies or antigens, or polymerized antigens. In particular said layer may be considered as monolayer with an approximate thickness of about 5 nm. The layer may be "complete" (particles saturated with antibodies) or, "incomplete" (i.e. less antibodies are used than the binding capacity of the particle would afford).

Depending on the particular analyte or sample to be assessed a skilled ready will be able to provide coated nanoparticles, in particular optimized as regards their size and amount of coating.

For example, if a high concentration analyte has to be assessed, for example like CRP, typically small particles may be used (e.g. 44 nm particles), fully saturated with antibody, as for example total IgG or IgY fractions, typically containing 3-20% analyte specific antibodies, the rest being non-binding antibodies, and low amounts if inert proteins like albumin or transferrin. In order to increase the signal, as for example in CRP assays (so-called high sensitivity CRP assays), it may be advantageous to increase the particle size significantly, often to a size of 60 to 100 nm and even 150 nm and higher, and/or use affinity purified antibodies and/or to have up to 100% of the antibodies on the surface in the form of binding antibodies, e.g. affinity purified antibodies or monoclonal antibodies.

However, if the method of the invention is used for low-concentrated analytes, e.g. Cystatin C, insulin or choriongonadotropins, larger particles with antigen affinity purified antibodies or other antibody preparations with close to 100% binding molecules may be used in particular.

Therefore, a wide range of particle sizes and a wide percent range of amount and specificity of coating material will be relevant in the present invention, dependant on the concentration of the analyte to be measured. Often also a combination of large sized particles, e.g. with a mean diameter of 870 to 250 nm with high affinity antibodies is used in combination with smaller particles—typically 40-60 nm—with lower affinity, combining a high sensitivity (provided by the high affinity larger particles) and a high capacity (provided by the low affinity smaller particles with larger surface per gram particles and carrying a lot of antibodies).

If said nanoparticles are coated completely, they are coated with 1 to 50%, in particular 2 to 40% or, or 6 to 30% or 8 to 25% antibody per total weight of the nanoparticle-antibody conjugate.

If said nanoparticles are coated incompletely, they are coated with about 5 to 35%, in particular 10 to 30% or 15 to 25% antibody per total weight of the nanoparticle-antibody conjugate.

In a further embodiment, the nanoparticles may be coated with a mixture of antibody and inert, preferably hydrophilic, protein. For example, from 20 to 90%, or 35 to 80%, or 40 to 70% of the total protein bound to the surface of the nanoparticles are constituted by the anti-analyte antibody. Such particles may carry antibodies in an amount, which is less than the amount of antibodies theoretically attachable to the particles according to the binding capacity of said non-coated particles. At the same time areas of the particle surface not covered by antibody molecules are saturated with inert, for example hydrophilic protein, or antibody molecules without affinity for the analyte. For example, mixtures of one or more hydrophilic inert proteins with the required anti-analyte antibodies may be present during the conjugation/binding of the antibodies to the nanoparticles. Non-limiting examples for such hydrophilic, inert proteins are limpet hemocyanin, haptoglobin, bovine transferrin, albumin and other water-soluble proteins.

Said non-coated nanoparticles may essentially be made of any conventional material, like latex, polystyrene, polyvinyl chloride, epoxy resin, polyvinylidene chloride, poly-alpha-naphthyl methacrylate, polyvinylnaphthalene, and corresponding copolymers thereof, gold colloids or other metal colloids, colloid carbon or other colloid materials.

Other suitable particle materials are available in the art and a skilled reader will be in a position to make an appropriate selection.

According to a further embodiment of the claimed method the turbidity change may be measured via the change in the said assay mixture's absorbance of light at a wavelength in the range of 300 to 700 or 300 to 800 nm, and at a temperature in the range of 10 to 50 degree Celsius, and after a period of 5 to 600 seconds, as for example 10, 25, 40, 120, 260, 300 or 600 seconds, of reaction time.

2. Anti-Analyte Antibodies

The present invention is not limited with respect to the particular anti-analyte antibody (or more generally immunoglobulin or antigen binding molecule) to be used for detecting an binding the analyte of interest. As explained in more detail below, binding antibodies or binding fragments derived there from may be applied. Also said antigen binding molecules may be of different animal (mammalian or non-mammalian) origin.

In a particular embodiment, however, said antigen binding molecule is of non-mammalian origin, in particular avian origin, if a mammalian antigen or a set of different, antigenically related mammalian antigens has to be analyzed. This may have the added advantage that such binding molecules of non-mammalian origin may show more similar affinities to antigens (analytes) of different mammalian origin.

2.1 Polyclonal Antibodies

Polyclonal antibodies can be prepared by methods well known in the art, such as those described for example by Chase, M. W., 1967, in "Methods of Immunology and Immunochemistry", ed. Williams, A. et al., M. W., pp. 197-209, Academic Press, New York. Briefly, animals of a suitable species (for example rabbits, goats, or sheep, or, avian species, in particular poultry, like hens) are repetitively immunized with purified antigen in an appropriate adjuvant, for example Freund's complete or incomplete adjuvant. After immunization the animals are bled and the polyclonal antibodies are purified by methods such as for example ammonium sulfate or ammonium chloride precipitation, anionic exchange chromatography, immunoaffinity chromatography, and/or affinity chromatography.

To achieve a sufficient turbidimetric signal in sensitive assays where the concentration of the analyte molecules in the sample is low, antibodies of high avidity are preferred. Since polyclonal antibodies comprise many different antibody molecules, an affinity constant cannot be calculated, however high avidity and affinity was obtained by conventional polyclonal antibody techniques. Preferred results were obtained when avian antibodies were used. The avian antibodies may be prepared according to the methods described in Larsson A, Baaloew R-M, Lindahl T, and Forsberg P-O in Poultry Science 72:1807-1812, 1993. It is contemplated that the avians being genetically more distinct from humans or mammalian in general are able to generate antibodies towards mammalian antigens that have a higher avidity than polyclonal mammalian antibodies.

Polyclonal avian antibodies routinely are obtained from egg yolk (and are therefore designated IgYs). Egg yolk, however, contains large amounts of lipids making their further use problematic. IgY can be isolated from egg yolk by using stepwise ammonium sulphate (for example 25 to 40%) and polyethylene glycol (PEG) precipitation. For initial purification also commercial IgY purification kits obtainable from Gallus Immunotch Inc, Cary, USA, or the Eggcellent Chicken IgY Purification Kit, obtainable from Pierce, Rockford, USA may also be employed considering the manufacturer's instructions. Avian IgY antibodies their production, purification and use are also described in the Dissertation by D. Calander, 2002, Uppsala University (ISBN 91-554-5227-2), incorporated by reference.

IgY is the major low molecular weight serum immunoglobulin found in egg laying animals and differs from its mammalian counterpart IgG in several respects. The heavy (H) chain is larger and antigenically different from its mammalian counterpart. The molecular weight of the light (L) chain is lower than that of its mammalian counterpart. The overall weight of IgY (about 167 kDa) is somewhat higher than that of IgG (about 160 kDa). Its H chain (about 65.1 kDa) is composed of one variable and four constant regions; its L chain (about 18.8 kDa) is composed of one variable and one constant region. Its Fc region mediates most biological effector functions in chicken.

Furthermore, the avidity of polyclonal antibodies may be further increased by using antibodies that were purified by the use of antigen affinity purification methods, for example according to the teaching in "Affinity Purification of Proteins" downloaded from www.piercenet.com (April 2006) and incorporated by reference.

Increased avidity may be observed when 20% of the antibodies used had been antigen affinity purified, even more increase was observed when 50% of the antibodies had been antigen affinity purified and even more when more than 75%, like 75 to 100% of the antibodies had been obtained by antigen affinity purification methods.

For affinity purification of avian polyclonal anti-mammalian antigene antibodies a suitable mammalian antigene affinity column has to be prepared. Purified mammalian antigene is fixed by a standard protocol to a suitable solid supports as for example are Sepharose or Affi-gel, activated to covalently the antigen to the support (suitable activated solid supports are for example available from Pierce, Rockford, USA). An affinity column is then prepared from said antigen-carrying resin.

Successful affinity purification of antibody depends on effective presentation of the relevant epitopes on the antigen to binding sites of the antibody. If the antigen is small and immobilized directly to a solid support surface by multiple chemical bonds, important epitopes may be blocked or sterically hindered, prohibiting effective antibody binding. Therefore, it is best to immobilize antigens using a unique functional group (e.g., sulfhydryl on a single terminal cysteine in a peptide) and to use an activated support whose reactive groups occur on spacer arms that are several atoms long. For larger antigens, especially those with multiple sites of immobilization, the spacer arm length becomes less important since the antigen itself serves as an effective spacer between the support matrix and the epitope.

Little variation normally exists among typical binding and elution conditions for affinity purification of antibodies because at the core of each procedure is the affinity of an antibody for its respective antigen. Since antibodies are designed to recognize and bind antigens tightly under physiologic conditions, most affinity purification procedures use binding conditions that mimic physiologic pH and ionic strength. The most common binding buffers are phosphate buffered saline (PBS) and Tris buffered saline (TBS) at pH 7.2 and 1.5 M NaCl (premixed buffer packs are for example available from Pierce, Rockford, USA). Once the antibody has been bound to an immobilized antigen, additional binding buffer is used to wash unbound material from the support. To minimize non-specific binding, the wash buffer may contain additional salt or detergent to disrupt any weak interactions.

Specific, purified antibodies are eluted from an affinity resin by altering the pH and/or ionic strength of the buffer (common elution buffers are for example available from Pierce, Rockford, USA). Antibodies in general are resilient proteins that tolerate a range of pH from 2.5 to 11.5 with minimal loss of activity, and this is by far the most common elution strategy. In some cases an antibody-antigen interaction is not efficiently disrupted by pH changes or is damaged by the pH, requiring that an alternate strategy be employed.

An example for an affinity purification protocol is given below:

Step 1: Wash the column (~1 ml resin bed) to remove residual protein before each use using 10 column volumes of the following sequence of buffers:
0.2 M glycine, pH 2.8~10 ml
0.1 M NaHCO$_3$, pH 8.5, 0.5 M NaCl~10 ml
Repeat the cycle with the above buffers twice. Then equilibrate the column in TTBS buffer (0.3 M NaCl, 20 mM Tris/Cl, pH 7.8, 0.1% (v/v) TWEEN® 20 and 0.01% NaN$_3$) containing NaCl adjusted to 0.5 M.

Step 2: Add to 10 ml aliquot of crude antibody preparation, 1 ml 10×TTBS and 0.55 ml 4 M NaCl. Centrifuge the mixture to remove any precipitate.

Step 3: Absorb the antibody batchwise by transferring the affinity resin to the tube (a 15 ml tube) with the serum. Incubate in the cold room. Alternatively, one can apply the serum to the column using a slow flow rate. Manually collected fractions are obtained. Collect the phase that passes through the column and re-apply it a second time using a slow flow rate.

Step 4: Wash the column extensively with TTBS+NaCl to 0.5 M until the A$_{280}$ is less than 0.02. Collect 10 ml fractions of the washes and check the A$_{280}$ of the fractions.

Step 5: Elute the antibody using 0.2 M glycine, pH 2.8, containing 0.02% NaN$_3$. Elute using 1 ml aliquots of buffer. Collect fractions into 1.5 ml microfuge tube containing 50 ml 1 M Tris, pH 8.5. This neutralizes the acidic elution buffer soon after the protein is eluted. Collect at least 10 fractions. This is usually sufficient to remove the antibody. Read the A$_{280}$ of each fraction using an appropriate blank (i.e., 1 ml glycine buffer plus 50 ml 1 M Tris).

Step 6: Pool the appropriate fractions. Get an A$_{280}$ of the pools and store antibodies at 4° C. or consider freezing (−70° C.) in aliquots in the presence of 50% glycerol.

Step 7: Wash the column by washing extensively with the 0.2 M glycine, pH 2.8 buffer, followed by TTBS.

2.2 Monoclonal Antibodies

Polyclonal antibodies are often more preferred than monoclonal antibodies in particle-enhanced turbidimetric assays. Polyclonal antibodies are inherently reactive to many different epitopes on the antigens (or analytes) (contrary to monoclonals), and therefore more easily create cross-bindings and networks between the antigens molecules per se, and between the antigens and the particles to which the antibodies are immobilized. In contrast, monoclonal antibodies generally bind to one type of epitopes only, which makes it more difficult to form cross-bindings and networks. The diagnostic industry often prefers, however, the use of monoclonal antibodies, because they are easier to standardized and to quality control to a predefined standard, especially over a product life-time of many years. There are, therefore, good examples on the use of monoclonal antibodies for particle enhanced turbidimetric immunoassays, especially when there are antigenic characteristics favoring the use of monoclonal antibodies. Eda et al. in "Development of a New Microparticle-Enhanced Turbidimetric Assay for C-reactive protein With Superior Features in Analytical Sensitivity and Dynamic range", J. Clin. Lab. Analysis, 12: 137-144 (1998) describes the use of two different monoclonal antibodies and two different micro particles. CRP is especially favorable for the use of monoclonals, because the CRP molecule is a pentamer of identical subunits—and therefore carries five replicates of all epitopes (Pepys M B et al, Adv. Immunol. 34:141-212 (1983)), which makes the use of monoclonal antibodies much easier. However, also with monomeric and smaller proteins like Cystatin C, cocktails of different monoclonal antibodies may be used in cocktails of different monoclonal antibodies, especially when they are composed of many different monoclonal antibodies with high affinity to the antigen and will result in good immunoassays.

Monoclonal anti mammalian antigene antibodies also can be prepared by methods well known in the art, as for example those described by G. Köhler at al., 1975, Nature 256, 495, G. Galfre et al., 1981, Meth. Enzymol. 73, 3-46, or R. Kennet, 1980, in: "Hybridomas: a new dimension in biological analysis", ed. R. Kennet et al., Plenum Press, New York & London. Spleen cells or peripheral blood cells from antigene immunized mice or rats are fused with a myeloma cell line, using for instance the polyethylene fusion method. After fusion the cells are grown under suitable conditions, for example on culture plates and a selection of correctly fused cells is performed using for example the hypoxanthine/aminopterin/thymidine (HAT) selection method. Antibody producing cell lines are identified by methods such as EIAs, RIAs or agglutination assays. After identification of the antibody producing cell line, the cells are repeatedly subcloned, as for example by the method of limited dilution, to guarantee that the new growing cell line derives from one single cell.

2.3 Chimeric Antibodies

Chimeric anti mammalian antigene antibodies can be obtained by methods well known in the art such as that described by G. L. Boulianne et al., 1984, Nature 312, 643-645. The procedure can be briefly described as follows. The DNA of the antigen-binding site from a monoclonal antibody of one species or parts thereof are transferred to the DNA of the antibody framework of another antibody of a different species. This new construct is cloned into an expression vector, which is transferred to the corresponding expression system to produce the antibody.

2.4 Recombinant Antibodies

Recombinant anti mammalian antigene antibodies can be obtained without using animal vehicles by methods known in the art, such as those described by G. Winter et al., 1991, Nature, 349, 293 or J. S. Huston et al., 1988, Proc. Natl. Acad. Sci. USA, 85, 5879. Those methods involve the following steps: introduction of DNA (cDNA or synthetic DNA) coding for an antibody or fragments thereof into a host cell, for example *E. coli*, fungi, yeast, plants or eucaryotic cells, selection of antibodies with the desired specificity and affinity and expressing the antibody or fragment thereof in the corresponding expression system.

2.5 Antibody Fragments

Antibody fragments like Fab-, Fab'-, and F(ab')$_2$-fragments of polyclonal antibodies, monoclonal antibodies of any species (including chimeric antibodies and or recombinant antibodies) can be prepared by methods well known in the art, such as those described for example by A. Nissonoff et al., 1960, Arch Biochem Biophys, 89, 230, or R. P. Porter, 1959, Biochem J, 73, 119, or E. Harlow et al, 1988, in "Antibodies—A Laboratory Manual", 626-631, Cold Spring Harbour Press, New York, USA.

2.6 Antibodies Obtained from Library Screenings

In vitro methods also can be used to make the antibodies applicable in a method of the invention, wherein an antibody library is screened to identify an antibody having the desired binding specificity. Methods for such screening of recombinant antibody libraries are well known in the art and include methods described in, for example, Ladner et al. U.S. Pat. No. 5,223,409; Kang et al. PCT Publication No. WO 92/18619; Dower et al. PCT Publication No. WO 91/17271; Winter et al. PCT Publication No. WO 92/20791; Markland et al. PCT Publication No. WO 92/15679; Breitling et al. PCT Publication No. WO 93/01288; McCafferty et al. PCT Publication No. WO 92/01047; Garrard et al. PCT Publication No. WO 92/09690; Fuchs et al. (1991) *Bio/Technology* 9:1370-1372; Hay et al. (1992) *Hum Antibod Hybridomas* 3:81-85; Huse et al. (1989) *Science* 246:1275-1281; McCafferty et al., Nature (1990) 348:552-554; Griffiths et al. (1993) *EMBO J.* 12:725-734; Hawkins et al. (1992) *J Mol Biol* 226:889-896; Clackson et al. (1991) *Nature* 352:624-628; Gram et al. (1992) *PNAS* 89:3576-3580; Garrad et al. (1991) *Bio/Technology* 9:1373-1377; Hoogenboom et al. (1991) *Nuc Acid Res* 19:4133-4137; and Barbas et al. (1991) *PNAS* 88:7978-7982, US patent application publication 20030186374, and PCT Publication No. WO 97/29131, the contents of each of which are incorporated herein by reference.

The recombinant antibody library may be from a subject immunized with the analyte, or a portion of the analyte. Alternatively, the recombinant antibody library may be from a naïve subject, i.e., one who has not been immunized with the analyte. Antibodies are selected by screening the recombinant antibody library with the peptide comprising the analyte to thereby select those antibodies that recognize analyte. Methods for conducting such screening and selection are well known in the art.

Antibodies applicable in a method of the present invention can also be generated using various phage display methods known in the art. In phage display methods, functional antibody domains are displayed on the surface of phage particles, which carry the polynucleotide sequences encoding them. In a particular, such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., J. Immunol. Methods 182:41-50 (1995); Ames et al., J. Immunol. Methods 184:177-186 (1995); Kettleborough et al., Eur. J. Immunol. 24:952-958 (1994); Persic et al., Gene 187 9-18 (1997); Burton et al., Advances in Immunology 57:191-280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies including human antibodies or any other desired antigen binding fragment, and expressed in any desired host, including mammalian cells, insect cells, plant cells, yeast, and bacteria. For example, techniques to recombinantly produce Fab, Fab' and F(ab')$_2$ fragments can also be employed using methods known in the art such as those disclosed in PCT publication WO 92/22324; Mullinax et al., BioTechniques 12(6):864-869 (1992); and Sawai et al., AJRI 34:26-34 (1995); and Better et al., Science 240:1041-1043 (1988) (said references incorporated by reference in their entireties).

Examples of techniques, which can be used to produce single-chain Fvs and antibodies include those described in U.S. Pat. Nos. 4,946,778 and 5,258,498; Huston et al., Methods in Enzymology 203:46-88 (1991); Shu et al., PNAS 90:7995-7999 (1993); and Skerra et al., Science 240:1038-1040 (1988).

Alternative to screening of recombinant antibody libraries by phage display, other methodologies known in the art for screening large combinatorial libraries can be applied to the identification of dual specificity antibodies of the invention. One type of alternative expression system is one in which the recombinant antibody library is expressed as RNA-protein fusions, as described in PCT Publication No. WO 98/31700 by Szostak and Roberts, and in Roberts, R. W. and Szostak, J. W. (1997) *Proc. Natl. Acad. Sci. USA* 94:12297-12302. In this system, a covalent fusion is created between an mRNA and the peptide or protein that it encodes by in vitro translation of synthetic mRNAs that carry puromycin, a peptidyl acceptor antibiotic, at their 3' end. Thus, a specific mRNA can be enriched from a complex mixture of mRNAs (e.g., a combinatorial library) based on the properties of the encoded peptide or protein, e.g., antibody, or portion thereof, such as binding of the antibody, or portion thereof, to the dual specificity antigen. Nucleic acid sequences encoding antibodies, or portions thereof, recovered from screening of such libraries can be expressed by recombinant means as described above (e.g., in mammalian host cells) and, moreover, can be subjected to further affinity maturation by either additional rounds of screening of mRNA-peptide fusions in which mutations have been introduced into the originally selected sequence(s), or by other methods for affinity maturation in vitro of recombinant antibodies, as described above.

In another approach the antibodies of the present invention can also be generated using yeast display methods known in the art. In yeast display methods, genetic methods are used to tether antibody domains to the yeast cell wall and display them on the surface of yeast. In particular, such yeast can be utilized to display antigen-binding domains expressed from a repertoire or combinatorial antibody library (e.g., human or murine). Examples of yeast display methods that can be used to make the antibodies of the present invention include those disclosed Wittrup, et al. U.S. Pat. No. 6,699,658 incorporated herein by reference.

The following non-limiting examples illustrate in a non-limiting manner the method of the invention.

EXPERIMENTAL PART

Example 1

Human C-Reactive Protein Immunoassay Reagents and Method a) Immunoparticles:

Antigen affinity purified anti-human C-reactive protein chicken antibodies, prod. no. A13CRP, were delivered from Norwegian Antibodies AS, Norway, and dialysed against 10 mM borate buffer 10 mM sodium chloride pH=8.5. White Chloromethyl Latex, Product No. C29792, chloromethyl latex, 4% w/v, particle size 0.067 µm was delivered from InVitrogen, Belgium, and washed by repeated centrifugation in water. 375 mg of said chloromethyl latex was suspended in 10 ml water, and mixed with 100 mg of said antibodies in 20 ml 10 mM borate buffer (10 mM sodium chloride, pH=8.5), and incubated at 37° C. for 4 hours. Thereafter 1 ml of 10 mM borate buffer (10 mM sodium chloride, 100 mM glycine, pH=8.5) was added, and the mixture was kept at room temperature over night. Thereafter the mixture was extensively dialysed in a spectra/por dialysis sack with a mean pore-size of 1,000,000 kilodalton against 30 mM TRIS buffer (15 mM sodium chloride, 0.1% TWEEN® 20, 3 mg/ml egg albumin, pH=8.5). After the dialysis, the mixture was suspended in, 8 mM TRIS buffer, 5 mM sodium chloride, 0.01% TWEEN® 20, 0.5 mg/ml egg albumin, pH=8.5) to a total volume of 30 ml.

b) Assay Buffer:

A solution of purified water was made from 5 g/l PEG 6000, 0.5 g/l TWEEN® 20, 45 mM 4-morpholinepropanesulfonic acid, and 9 g/l NaCl, in order to obtain the assay buffer (pH=7.2).

c) Assay Method:

In a Hitachi 917 instrument, 2 µl sample to be tested was mixed with 150 µl assay buffer. After 5 minutes, 150 µl of immunoparticles suspension (see above) was added. Immediately after the mixing, the absorbance at 570 nm was read, and absorbances were read again 2.5 minutes after the mixing of the immunoparticles.

The instrument kept all the reagents at 37° C. during the performance of the assay.

The instrument reported the increase in absorption at 570 nm (called the primary reading wavelength) minus the increase in the absorption at 800 nm (called the secondary reading wavelength) over the time period. The instrument uses a secondary reading wavelength mainly to compensate for instrument variations over time, e.g. slight fluctuations in electric voltage supply.

Presence of human C-reactive protein in the sample resulted in an increase in the difference between the absorbance at the start point and at the end point, caused by aggregation of the immunoparticles (see more details below).

If an increased sensitivity of the assay was required, absorbance at 546 nm was chosen instead of 570 nm, if a higher capacity of the assay was needed, absorbance at 700 nm was chosen instead of 570 nm.

Example 2

Preparing a Secondary Calibrator for Human CRP Assays

This example illustrates the principle of value assignment, in particular how secondary calibrator values may be derived from primary calibrators.

A liquid pool of delipidated human serum enriched with CRP was made as detailed in c) below and this pool (which was later used as a secondary calibrator for CRP assays) was assigned a CRP value by turbidimetry using a very precise transfer protocol (as described in Blirup-Jensen S, Myron Johnson A, Larsen M. Protein standardization IV: Value transfer procedure for the assignment of serum protein values from a reference preparation to a target material. Clin Chem Lab Med 2001; 39:1110-22) and ensuring traceability to the International Reference Preparation CRM 470 (as described in Baudner S, Bienvenu J, Blirup-Jensen S, Carlström A, Johnson A M, Milford Ward A, et al. "The certification of a matrix reference material for immunochemical measurement of 14 human serum proteins CRM 470. Community Bureau of Reference, Commission of the European Communities, Final Report, EUR 15243 EN, 1993: 1-186") using the following method:

a) A vial of the primary calibrator CRM470 material ERM-DA472/IFCC comprising human C-reactive protein (CRP) 41.8±2.5 mg per litre was delivered from IRMM, European Commission, Joint Research Centre Institute for Reference Materials and Measurements, The Reference Materials Unit, Geel, Belgium. This was the primary human CRP calibrator material.

b) Six linear dilutions (6.96 mg/l, 13.93 mg/l, 20.9 mg/l, 27.87, 34.85 mg/l and 41.8 mg/l) of the reference material according to a) was made according to point 1 in the protocol as prescribed in column 2, page 1113 of Blirup-Jensen S, Myron Johnson A, Larsen M. "Protein standardization IV: Value transfer procedure for the assignment of serum protein values from a reference preparation to a target material. Clin Chem Lab Med 2001; 39:1110-22").

c) A secondary calibrator material was made from normal human serum, ultracentrifuged to remove lipid particles and other particles from the serum, and highly purified human C-reactive protein, delivered from Scipac Ltd., U.K., prod. No. P100-7, was added to obtain approximately 400 mg human CRP per litre.

d) Dilutions ¹⁄₁₀, ¹⁄₁₂, ¹⁄₁₅, ¹⁄₂₀, ¹⁄₃₀ and ¹⁄₆₀ of the secondary calibrator material according to c) was made, aiming at concentrations corresponding to the dilutions that had been made by the primary calibrator material according to b) above.

e) A calibration run was performed using the C-reactive protein assay according to Example 1 above, and using the 6 dilutions of the primary calibrator material.

f) A measurement run of the dilutions of the secondary calibrator material according to d) was performed using the C-reactive protein assay according to Example 1 and using the calibration obtained from e) above (where the 6 dilutions of the primary calibrator material had been used).

g) The results were interpolated on the calibration curve obtained in the calibration run according to e) above, and the resulting values of the different dilutions of the secondary calibrator material was noted.

Figure 3:
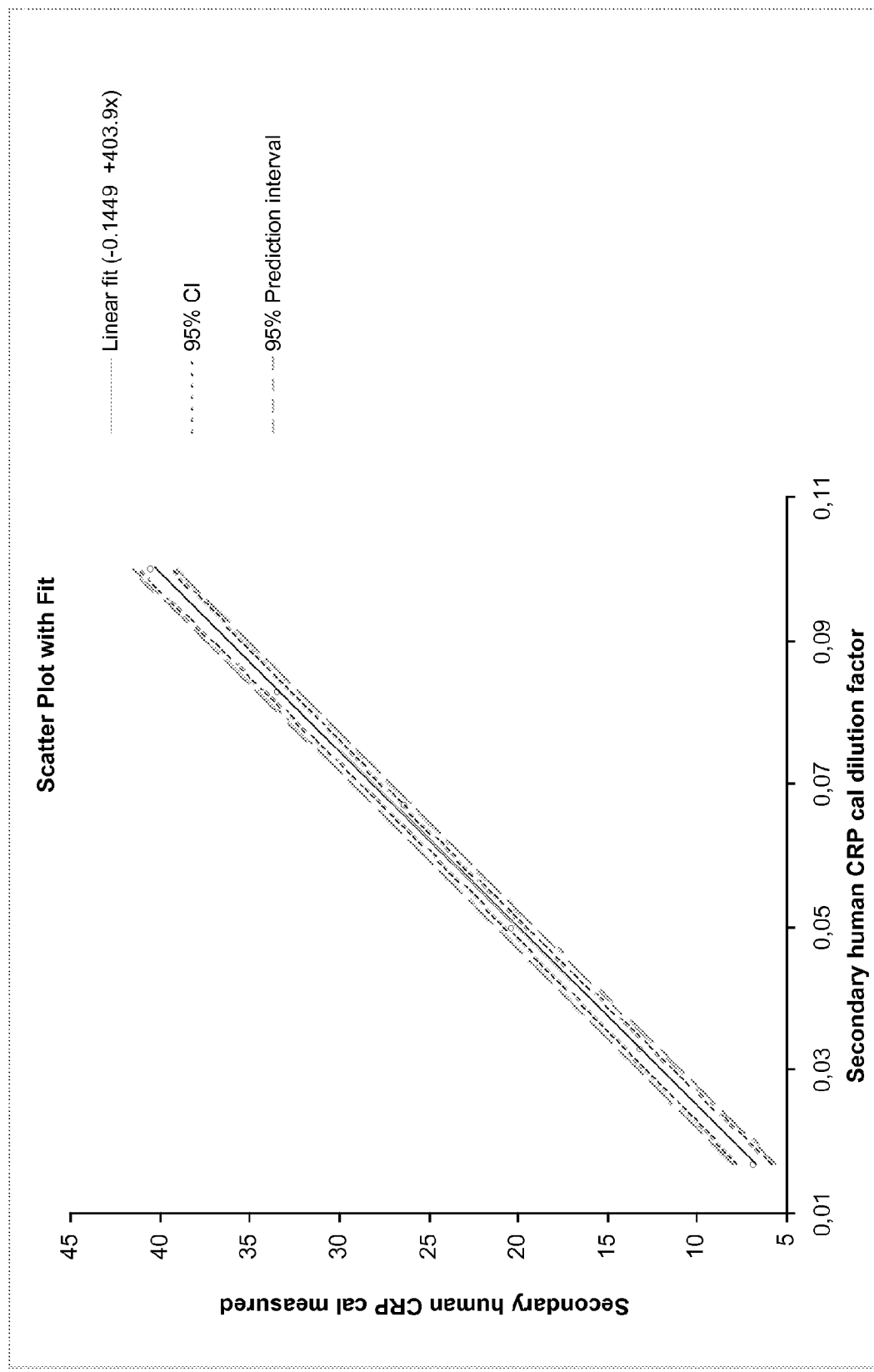
FIGS. 3 to 9 illustrate data plots obtained according to specific examples of analytical methods of the present invention as further explained in the following experimental section. In each Figure a linear fit of the data points (full line), a 95% confidence interval (dotted lines) and a 95% prediction interval (dashed lines) are shown.

| Primary human CRP (mg/l) | Secondary human CRP measured (mg/l) | Secondary human CRP cal dilution |
|---|---|---|
| 6.96 | 6.8 | 0.017 |
| 13.93 | 13.2 | 0.033 |
| 20.90 | 20.5 | 0.050 |
| 27.87 | 26.3 | 0.067 |
| 34.85 | 33.4 | 0.083 |
| 41.80 | 40.5 | 0.100 | h) The resulting concentration value points of the different dilutions of the secondary calibrator material were plotted against the dilution factor, a best fit correlation curve (using least square value fit) was drawn through the resulting points (see FIG. 3). The concentration of the undiluted secondary calibrator material could be calculated from the curve where the dilution factor was 1.0. A value of 404 mg CRP/l with a 95% confidence interval of 389 to 418 mg/l was obtained.

Example 3

Preparing a Secondary Calibrator Material for Canine C-Reactive Protein Assays, and Assigning Said Secondary Calibrator Material with a Calibration Value for Canine Samples, Said Secondary Calibrator Material Comprising Human C-Reactive Protein (but No Canine C-Reactive Protein)

a) A primary canine C-reactive protein calibrator was delivered from Tridelta Development Ltd, Ireland, (prod no TP810-CAL), comprising 100.8 mg canine CRP per litre.
b) Six linear dilutions (100.8 mg/l, 80.6 mg/l, 60.5 mg/l, 40.3 mg/l, 20.2 mg/l and 10.1 mg/l) of the primary calibrator TP810-CAL was made according to point 1 in the protocol as prescribed in column 2, page 1113 of Blirup-Jensen S, Myron Johnson A, Larsen M. "Protein standardization IV: Value transfer procedure for the assignment of serum protein values from a reference preparation to a target material. Clin Chem Lab Med 2001; 39:1110-22".
c) The secondary calibrator (comprising human CRP) prepared according to Example 2c) was diluted to 100 mg/l, 80 mg/l, 60 mg/l, 40 mg/l, 20 mg/l and 10 mg/l.
d) A calibration run was performed using the dilutions of the canine primary calibrator material and described in step b) above and the CRP assay reagents and method described in Example 1.
e) A measurement run of the dilutions of the secondary calibrator (human CRP based) according to step c) above was performed using the C-reactive protein assay according to Example 1 with the calibration obtained when canine primary calibrator was used according to step d) above. The results were interpolated on the calibration curve obtained in the calibration run according to step d) above, and the resulting values (mg/l CRP) of the different dilutions of the secondary calibrator was noted.

Figure 4:
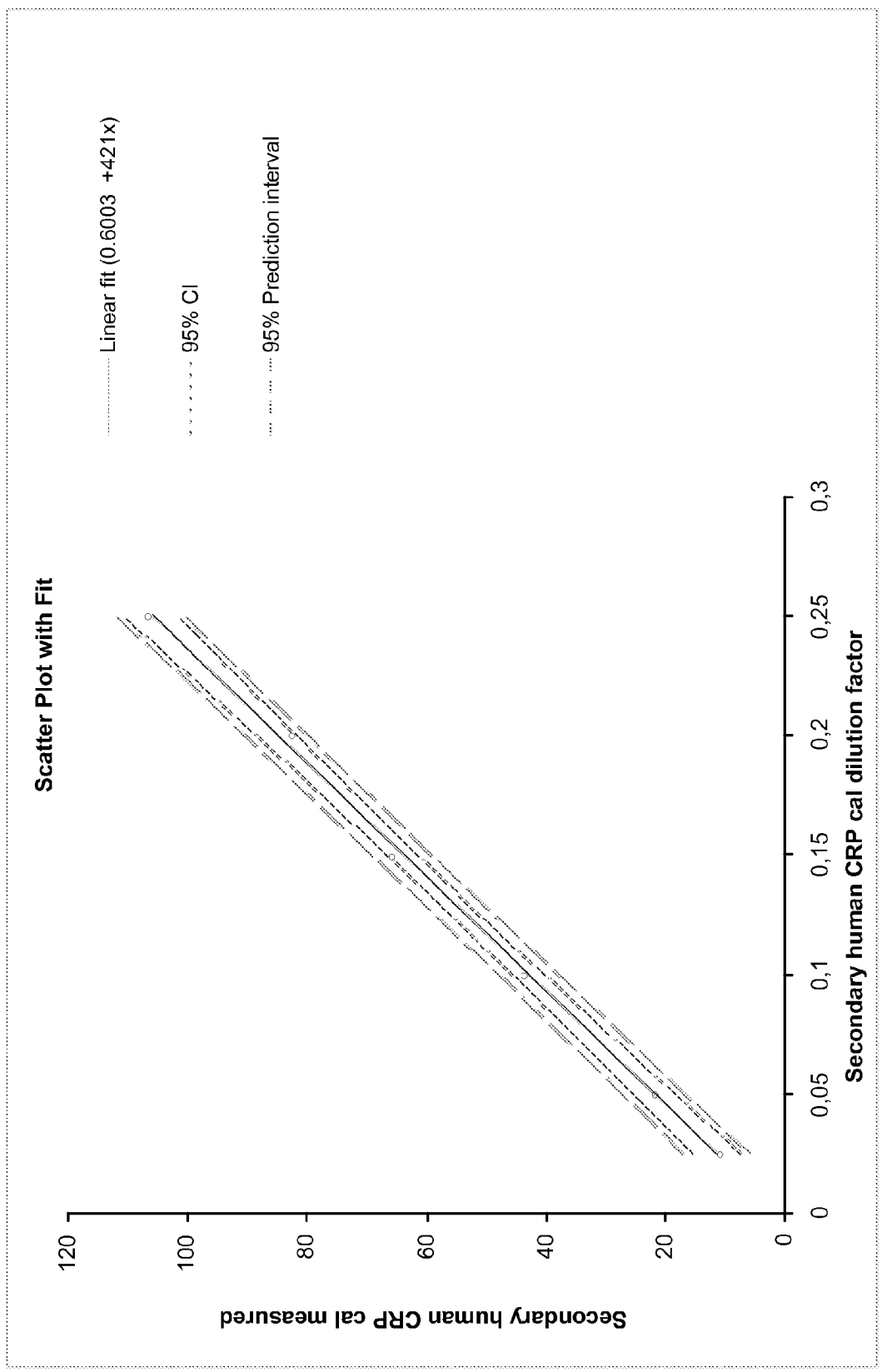

| Primary dog CRP calibrator (mg/l) | Secondary human CRP measured (mg/l) | Secondary human CRP cal dilution |
|---|---|---|
| 10.1 | 10.6 | 0.025 |
| 20.2 | 21.2 | 0.050 |
| 40.3 | 43.3 | 0.100 |
| 60.5 | 65.6 | 0150 |
| 80.6 | 82.3 | 0.200 |
| 100.8 | 106.6 | 0.250 | f) The resulting concentration value points of the different dilutions of the secondary calibrator was plotted against the dilution factor, a best fit correlation curve (using least square value fit) was drawn through the resulting points (see FIG. 4). The value of the undiluted secondary calibrator from Example 2c above could be calculated to 422 mg dog CRP per litre, with a 95% confidence interval from 398 to 445 mg/l. In this way, a calibration value for canine CRP was assigned to the secondary calibrator from Example 2c, although it comprises no canine CRP.

Example 4

A Canine CRP Assay without Presence of Canine CRP in the Calibrator Materials Using a Secondary Calibrator Material Comprising Human CRP (but No Canine CRP)

A canine CRP assay was made using the assay reagents and methods identical to Example 1, but with the use of the secondary CRP calibrator comprising human CRP but assigned with a value for canine CRP, as described in Example 3 above.

In this way, it was possible to produce an avian antibody based canine CRP assay using avian antibodies raised against human CRP and with a secondary calibrator based on human CRP, but with canine CRP values assigned, without presence of canine CRP in the secondary calibrator materials.

Example 5A

Preparing a Secondary Calibrator Material for Horse C-Reactive Protein Assays, And Assigning Said Secondary Calibrator Material with a Calibration Value for Horse Samples, Said Secondary Calibrator Material Comprising Human C-Reactive Protein (Primary Calibrator Based on Pure Horse CRP)

a) A primary horse C-reactive protein calibrator material was delivered from Kamiya Biomedical Company, Washington State, US.
b) Dilutions to 320, 160, 80, 40, 20 and 10 mg horse CRP per litre was made according to point 1 in the protocol as prescribed in column 2 page 1113 of Blirup-Jensen S, Myron Johnson A, Larsen M. "Protein standardization IV: Value transfer procedure for the assignment of serum protein values from a reference preparation to a target material." Clin Chem Lab Med 2001; 39:1110-22.
c) The secondary calibrator material from Example 2c was diluted to approximately 320, 160, 80, 40, 20 and 10 mg human CRP respectively.
d) A calibration run was performed using the dilutions of the horse primary calibrator material dilutions as described in step a) above with the CRP assay reagents and method described in Example 1.
e) A measurement run of the dilutions of the secondary calibrator material (comprising human CRP) according to step c) above was performed using the C-reactive protein assay according to Example 1 with the calibration obtained according to d) above using horse primary calibrator obtained according to step a) and b) above. The results were interpolated on the calibration curve obtained in the calibration run according to step d) above, and the resulting values in mg/l CRP of the different dilutions of the secondary calibrator material was noted.
f) The resulting concentration value points of the different dilutions of the secondary calibrator material was plotted against the dilution factor, a best fit correlation curve (using least square value fit) was drawn through the resulting points. The concentration of the undiluted secondary calibrator material could be calculated from the curve where the dilution factor was 1.0. In this way, a calibration value for horse CRP was assigned to the target material from Example 2c, although it comprises no horse CRP.

Example 5B

Figure 5:
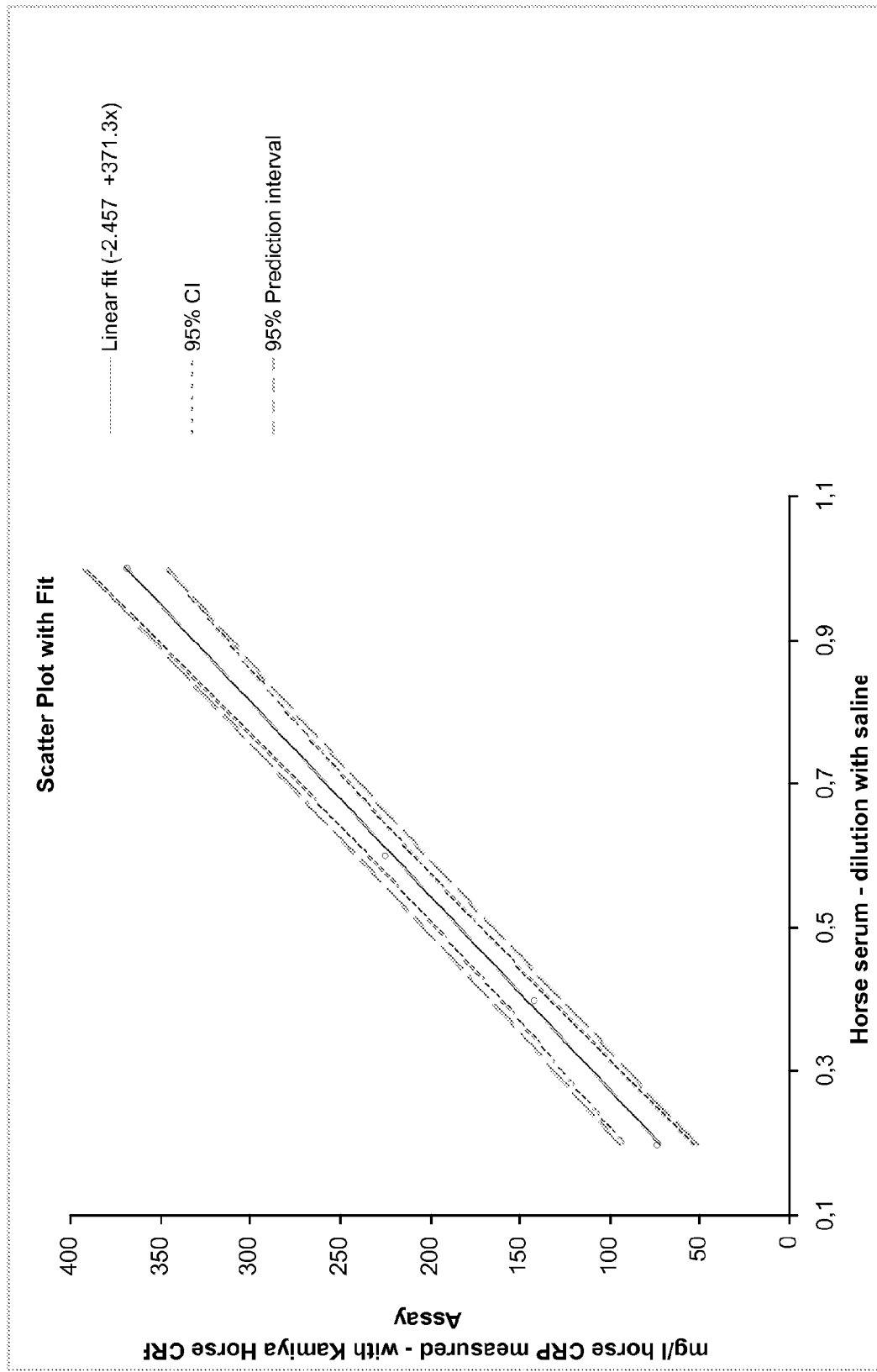

Preparing a Secondary Calibrator Material for Horse C-Reactive Protein Assays, and Assigning Said Secondary Calibrator Material with a Calibration Value for Horse Samples, Said Secondary Calibrator Material Comprising Human C-Reactive Protein. (Primary Calibrator Based on Horse Serum with Very High Horse CPR Value)

a) A primary horse C-reactive protein calibrator material was delivered from Kamiya Biomedical Company, Washington State, US.

b) A horse serum with very high CRP values was obtained from Prof. Bernt Jones, Department of Clinical Chemistry, College of Veterinary Medicine, Swedish University of Agricultural Sciences, Uppsala. The horse serum CRP content was measured in the following dilutions, using the Kamiya Horse CRP ELISA product (Catalog No KT-487):

| Horse Serum dilution with saline | horse CRP mg/l measured with Kamiya Horse CRP assay |
| --- | --- |
| 1 | 368 |
| 0.6 | 224 |
| 0.4 | 142 |
| 0.2 | 73 | and could be plotted against the dilution factor as shown in FIG. 5;

The horse serum material could then be assigned the value 369 mg horse CRP/l (95% confidence interval Of 342 mg/l to 401 mg/l), with a % CV of 4.0%, and constituted a horse CRP secondary calibrator containing horse CRP.

c) Dilutions of the horse serum based primary calibrator comprising horse CRP according to b) above was diluted in saline to 320, 160, 80, 40, 20 and 10 mg horse CRP per litre, according to point 1 in the protocol as prescribed in column 2 page 1113 of Blirup-Jensen S, Myron Johnson A, Larsen M. "Protein standardization IV: Value transfer procedure for the assignment of serum protein values from a reference preparation to a target material." Clin Chem Lab Med 2001; 39:1110-22.

d) The secondary calibrator material from Example 2c was diluted to approximately 320, 160, 80, 40, 20 and 10 mg human CRP per liter respectively.

e) A calibration run was performed using the dilutions of the horse secondary calibrator material dilutions as described in step b) above with the CRP assay reagents and method described in Example 1.

f) A measurement run of the dilutions of the secondary calibrator material (comprising human CRP) according to step d) above was performed using the C-reactive protein assay according to Example 1 with the calibration obtained according to e) above using horse serum based primary calibrator obtained according to step a), b) and c) above. The results were interpolated on the calibration curve obtained in the calibration run according to step e) above, and the resulting values in mg/l CRP of the different dilutions of the secondary calibrator material was noted.

Figure 6:
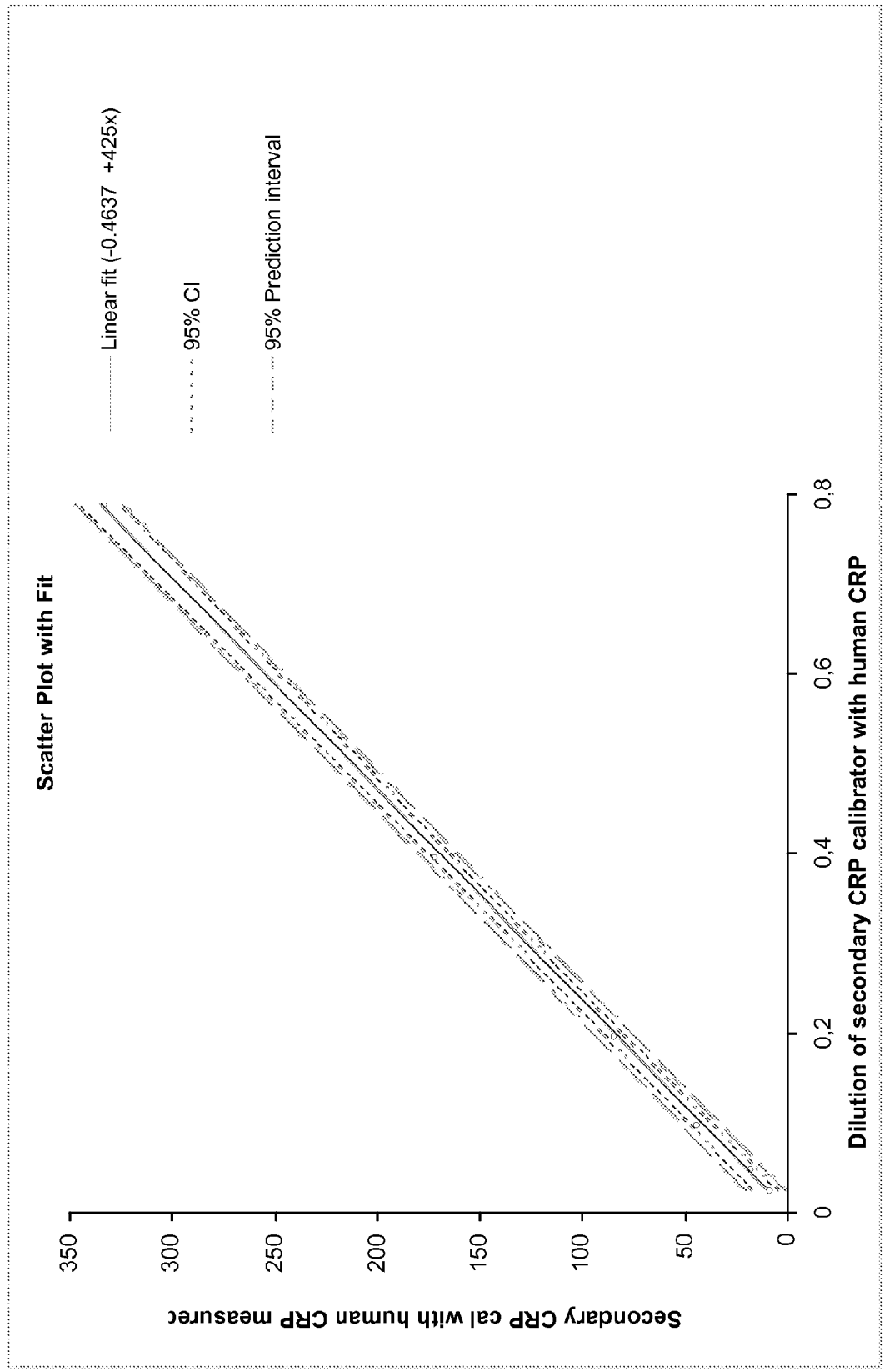

| Primary CRP cal with horse CRP (mg/l) | Secondary CRP cal with human CRP measured (mg/l) | Dilution of secondary CRP calibrator with Human CRP |
| --- | --- | --- |
| 320 | 333 | 0.79 |
| 160 | 172 | 0.396 |
| 80 | 84 | 0.198 |
| 40 | 44 | 0.099 |
| 20 | 18 | 0.0495 |
| 10 | 8 | 0.0248 | g) The resulting concentration value points of the different dilutions of the secondary calibrator material was plotted against the dilution factor (see FIG. 6), a best fit correlation curve (using least square value fit) was drawn through the resulting points. The concentration of the secondary calibrator material comprising human CRP from Example 2c could thus be assigned the value of 424 mg horse CRP/l with a confidence interval of 412-438 mg/l, although it comprises no horse CRP.

Example 6

A Horse CRP Assay without Presence of Horse CRP in the Calibrator Materials Using a Secondary Calibrator Material Comprising Human CRP (without Presence of Horse CRP in the Secondary Calibrator Material)

A horse CRP assay was made using the assay reagents and methods identical to Example 1, but with the use of the secondary calibrator comprising human CRP but assigned a value for horse CRP as described in Example 5 above.

In this way, it was possible to produce an avian antibody based horse CRP assay using avian antibodies raised against human CRP and with a calibrator based on human CRP, but with horse CRP values assigned, without presence of horse CRP in the secondary calibrator.

Further Modifications of the Previous Examples a) C-Reactive Protein Secondary Calibrators for Assays for Other Mammalian Species:

In Example 3 and 5, the secondary calibrator material from Example 2c above—comprising human C-reactive protein material—was assigned calibration values for canine and horse assays for C-reactive proteins, said assays being based on avian antibodies.

By purchasing or making primary C-reactive protein calibrator materials based on C-reactive proteins from other species, secondary calibrator materials like Example 2c above can be assigned values for calibration of C-reactive protein assays for a many different mammalian species, the said assays being based on avian antibodies towards mammalian CRP. The secondary calibrator value for each mammalian species can be assigned using assignment protocols as prescribed in column 2 page 1113 of Blirup-Jensen S, Myron Johnson A, Larsen M. "Protein standardization IV: Value transfer procedure for the assignment of serum protein values from a reference preparation to a target material. Clin Chem Lab Med 2001; 39:1110-22".

In this way, the secondary calibrator like the material in Example 2c above—which comprises human CRP and already has been assigned values for canine, horse, and human CRP, can also be assigned a value for rabbit C-reactive protein assays based on avian antibodies), using a rabbit C-reactive protein calibrator based on rabbit C-reactive protein (see for example cat. no KT-097 from Kamiya Biomedical Company, Seattle, US).

Furthermore, in this way, the secondary calibrator like the material in Example 2c above, can be assigned a value for pig C-reactive protein assays based on avian antibodies, using cat. no KT-184 from Kamiya Biomedical Company, Seattle, US, said catalog no. KT-184 comprises a pig C-reactive protein calibrator based on pig C-reactive protein.

Other primary calibrators comprising C-reactive proteins from other mammalian species can be used to assigned values to a secondary calibrator like the material in Example 2c above (which comprises human C-reactive protein).

If a solution of purified C-reactive protein from a species is used as a primary calibrator, a method like Blirup-Jensen "Protein Standardization II: Dry mass Determination Procedure for the Determination of the Dry Mass of a Pure Protein Preparation", Clin. Chem. Lab. Med. 2001, 39: 1090-1097, can be used to assign a concentration of C-reacting protein in the purified protein preparation (as the primary calibrator), and then a secondary calibrator—like the one described in Example 2c above—can be assigned a C-reactive protein concentration value using a protocol as prescribed in column 2 page 1113 of Blirup-Jensen S, Myron Johnson A, Larsen M. "Protein standardization IV: Value transfer procedure for the assignment of serum protein values from a reference preparation to a target material. Clin Chem Lab Med 2001; 39:1110-22".

Furthermore, the process of assignment of the value for the secondary calibrator comprising CRP from specified first mammalian species but for use as a calibrator for other mammalian species, may start out using a CRP calibrator material comprising CRP antigens from said first mammalian species in combination with other material (as for example serum) (in analogy to Example 5B).

b) a CRP Assay for Assaying CRP in Several Mammalian Species

A CRP assay which can be used for assaying CRP in many or all mammalian species, can be made using the assay reagents and methods identical to Example 1, and with the use of the secondary CRP calibrator described above, with calibrator values for CRP from many different mammalian species assigned to the secondary calibrator. Thus, in a preferred embodiment of the present invention, an avian antibody based CRP assay is made using antibodies raised against human CRP and with a calibrator based on human CRP, yielding valid results for CRP concentration determination of the CRP from samples from many different mammalian species, using the same reagents for samples for all species, provided the use of the correctly assigned calibrator value for the calibrator used (i.e. using the CRP calibrator value assigned for the same species from which the sample to be tested has been taken from).

Example 7

Human Urine Albumin Immunoassay Reagents and Method a) Immunoparticles:

Affinity purified anti-human albumin chicken antibodies, prod. no. A178-HSA, were delivered from Norwegian Antibodies AS, Norway, and dialysed against 10 mM borate buffer 10 mM sodium chloride pH=8.5. White Chloromethyl Latex Product No. C29792, Chloromethyl latex, 4% w/v particle size 0.067 μm was delivered from InVitrogen, Belgium, and washed by repeated centrifugation in water. 375 mg of said chloromethyl latex was suspended in 10 ml water, and mixed with 100 mg of said antibodies in 20 ml 10 mM borate buffer (10 mM sodium chloride pH=8.5), and incubated at 37° C. for 4 hours. Thereafter 1 ml of 10 mM borate buffer (10 mM sodium chloride, 100 mM glycine, pH=8.5) was added, and kept at room temperature over night. Thereafter the mixture was extensively dialysed in a spectra/por dialysis sack with a mean pore-size of 1,000,000 kilodalton against 30 mM TRIS buffer (15 mM sodium chloride, 0.1% TWEEN®20, 3 mg/ml egg albumin, pH=8.5). After the dialysis, the mixture was suspended in 8 mM TRIS buffer, 5 mM sodium chloride, 0.01% TWEEN® 20, 0.5 mg/ml egg albumin, pH=8.5 to a total volume of 30 ml.

b) Assay Buffer:

A solution of purified water was made from 5 g/l PEG 6000, 0.5 g/l TWEEN® 20, 45 mM 4-morpholinepropanesulfonic acid, and 9 g/l NaCl, in order to obtain the assay buffer (pH=7.2).

c) Assay Method:

In a Hiatchi 917 instrument, 2 μl urine sample to be tested was mixed with 150 μl assay buffer. After 5 minutes, 150 μl of immunoparticles suspension (see above) was added. Immediately after the mixing, the absorbance at 570 nm was read, and absorbances were read again 2.5 minutes after the mixing of the immunoparticles.

The instrument kept all the reagents at 37° C. during the performance of the assay.

The instrument recorded the increase in absorption at 570 nm (called the primary reading wavelength) minus the increase in the absorption at 800 nm (called the secondary reading wavelength) over the time period. (The instrument uses a secondary reading wavelength mainly to compensate for instrument variations over time, e.g. slight fluctuations in electric voltage supply)

Presence of human albumin protein in the sample resulted in an increase in the difference between the absorbance at the start point and at the end point, caused by aggregation of the immunoparticles (see more details below).

If an increased sensitivity of the assay was required, absorbance at 546 nm was chosen instead of 570 nm, if a higher capacity of the assay was needed, absorbance at 700 nm was chosen instead of 570 nm.

Example 8

Preparing a Secondary Calibrator Material for Human Albumin Urine Assays

A liquid pool of human urine enriched with human albumin and preserved with urine protein stabilizing agents as described by Anders Grubb in Scand J Clin Lab Invest 54(3): 199-206 was prepared. An albumin value assignment was carried out by turbidimetry using a very precise transfer protocol (as described in Blirup-Jensen S, Myron Johnson A, Larsen M. Protein standardization IV: Value transfer procedure for the assignment of serum protein values from a reference preparation to a target material. Clin Chem Lab Med 2001; 39:1110-22) and ensuring traceability to the International Reference Preparation CRM 470 (as described in Baudner S, Bienvenu J, Blirup-Jensen S, Carlström A, Johnson A M, Milford Ward A, et al. "The certification of a matrix reference material for immunochemical measurement of 14 human serum proteins CRM 470. Community Bureau of Reference, Commission of the European Communities, Final Report, EUR 15243 EN, 1993: 1-186") using the following method:
a) A vial of the primary calibrator material ERM-DA470 comprising 37.2 gram human albumin per litre was delivered from IRMM, European Commission, Joint Research Centre, Institute for Reference Materials and Measurements, The Reference Materials Unit, Geel, Belgium
b) Five dilutions (2 mg/l, 12 mg/l, 36 mg/l, 72 mg/l and 144, mg/l of the said primary calibrator material were made in said urine protein stabilizing agent according to point 1 in the protocol as prescribed in column 2 page 1113 of Blirup-Jensen S, Myron Johnson A, Larsen M. "Protein standardization IV: Value transfer procedure for the assignment of serum protein values from a reference preparation to a target material. Clin Chem Lab Med 2001; 39:1110-22".
c) A secondary calibrator material was made from highly purified human urine albumin, delivered from Scipac Ltd., U.K., prod. No. P140-0, diluted to approximately 400 mg human albumin per litre in said urine protein stabilizing agent. Dilutions 1/3, 1/6, 1/12, 1/36 and 1/130 of the secondary calibrator material was made in said urine protein stabilizing agent
d) A calibration run was performed using the albumin assay according to Example 7 above, and using the 6 dilutions of the primary calibrator material according to b) above
e) A measurement run of the dilutions of the secondary calibrator material according to d) was performed using the human albumin assay according to Example 7 using the calibration obtained in d) above (where dilutions of the primary calibrator material obtained according to step b) was used), and the results were interpolated on the calibration curve obtained in the calibration run according to d) above, and the resulting values of the different dilutions of the secondary calibrator was noted.

| Primary calibrator ERM-DA470 human albumin (mg/l) | Secondary calibrator Human albumin (mg/l) | Dilutions Secondary calibrator human albumin |
|---|---|---|
| 144 | 131 | 0.333 |
| 72 | 63.3 | 0.167 |
| 36 | 33.8 | 0.083 |
| 12 | 10.2 | 0.028 |
| 2 | 1.7 | 0.008 |

Figure 7:
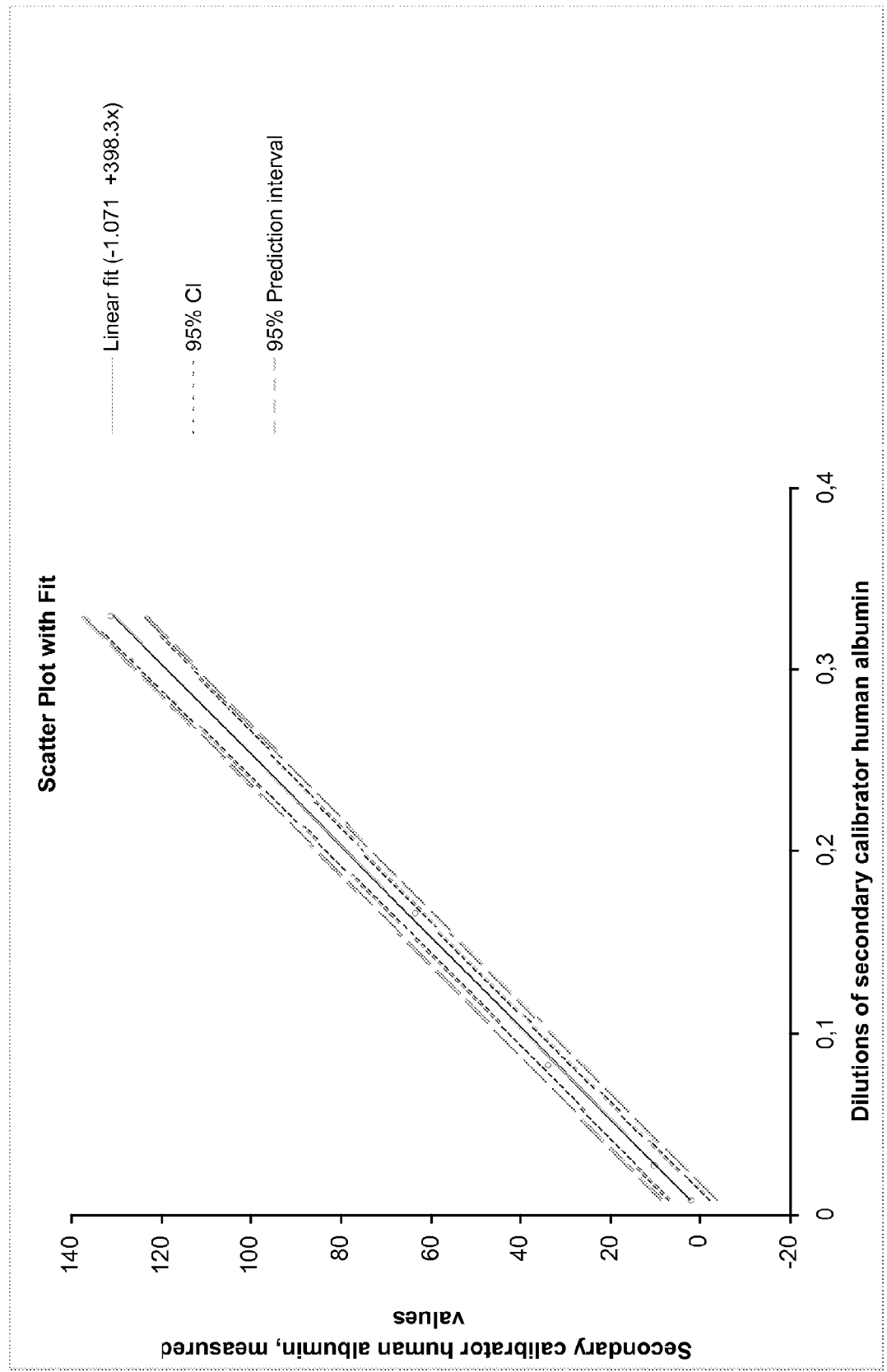

The resulting concentration value points of the different dilution of the secondary calibrator was plotted against the dilution factor, a best fit correlation curve (using least square value fit) was drawn through the resulting points (see FIG. 7).
The value assigned to the undiluted secondary calibrator could be calculated. A value of 397 mg albumin/l was obtained with a confidence interval of 377 mg/l to 418 mg/l.

Example 9

Making a Secondary Calibrator Material for a Bovine Urine Albumin (BUA) Assays, and assigning said secondary calibrator material with a value for bovine samples, Said Secondary Calibrator Material Comprising Human Albumin (and No Bovine Albumin)

a) A primary bovine albumin calibrator material was delivered from Bethyl Laboratories Inc, Texas, US, prod no No. (RC10-113), comprising 1000 mg bovine albumin per litre.

b) Five linear dilutions (200 mg/l, 100 mg/l, 40 mg/l and 20 mg/l and 10 mg/l of the RC10-113 was made according to point 1 in the protocol as prescribed in column 2 page 1113 of Blirup-Jensen S, Myron Johnson A, Larsen M. "Protein standardization IV: Value transfer procedure for the assignment of serum protein values from a reference preparation to a target material. Clin Chem Lab Med 2001; 39:1110-22".
c) The secondary calibrator material from Example 8c was diluted in said urine stabilizing agent to 200 mg/l, 100 mg/l, 40 mg/l, 20 mg/l and 10 mg/l
d) A calibration run was performed using the dilutions of the bovine primary calibrator material and described in Example 9b) and the albumin assay reagents and method described in Example 7.
e) A measurement run of the dilutions of the secondary calibrator material according to step c) above was performed using the albumin assay according to Example 7 with the bovine primary calibrator material obtained according to step c) above, and the results were interpolated on the calibration curve obtained in the calibration run according to step d) above, and the resulting values of the different dilutions of the secondary calibrator was noted.

Figure 8:
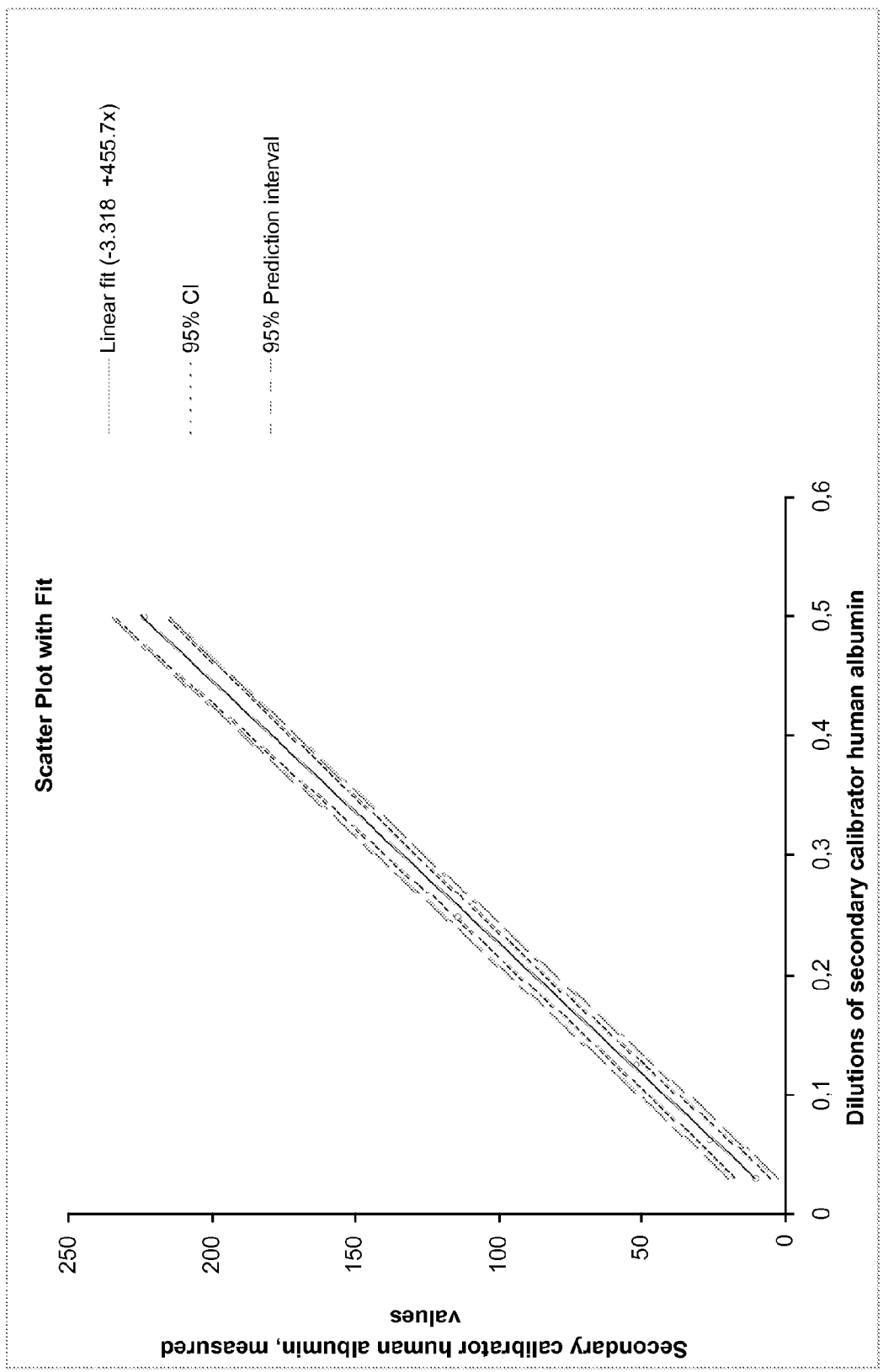

| Primary calibrator Bethyl BUA | Second calibrator Human albumin mg/l measured | Dilutions of Secondary human albumin calibrator |
|---|---|---|
| 200 | 223.5 | 0.50 |
| 100 | 113.7 | 0.25 |
| 40 | 51.4 | 0.125 |
| 20 | 26.1 | 0.063 |
| 10 | 10.3 | 0.031 | f) The resulting concentration value points of the different dilution of the secondary calibrator material was plotted against the dilution factor, a best fit correlation curve (using least square value fit) was drawn through the resulting points (see FIG. 8).
The value to assign to the secondary calibrator material could be calculated to 452 mg/l for bovine albumin of the secondary calibrator of Example 8c above, although it comprises no bovine albumin. The 95% confidence interval was 433 to 472 mg/l.

Example 10

A Urine Bovine Albumin Assay without Presence of Bovine Albumin in the Calibrators Using a Secondary Calibrator Comprising Human Albumin A bovine albumin assay was made using the assay reagents and methods identical to Example 7, but with the use of the secondary bovine albumin calibrator described in Example 9 (with a calibrator value obtained in Example 9f) above. In this way, it was possible to produce an avian antibody based bovine urine albumin assay using antibodies raised against human albumin and with a secondary calibrator based on human albumin, but with bovine albumin values assigned, without presence of bovine albumin in the secondary calibrator materials.

Example 11

Preparing a Secondary Calibrator Material for Porcine Urine Albumin Assays, and assigning said secondary calibrator material with a value for porcine urine samples, Said Secondary Calibrator Comprising Human Albumin a) A primary porcine albumin calibrator material >99% pure, Sigma A-4414 was delivered from Sigma Aldrich, US, or dried extensively in an dry vacuum atmosphere of several weeks. Thereafter it was weighed and dissolved in saline solution to 400 mg/l by weight control.

b) Dilutions to 100, 50, 20, 10 and 5 mg porcine albumin per litre was made in the said urine protein stabilizing agent and according to point 1 in the protocol as prescribed in column 2 page 1113 of Blirup-Jensen S, Myron Johnson A, Larsen M. "Protein standardization IV: Value transfer procedure for the assignment of serum protein values from a reference preparation to a target material." Clin Chem Lab Med 2001; 39:1110-22 c) The secondary calibrator material from Example 8c was diluted to 100, 50, 20, 10 and 5 mg human albumin per liter respectively.

d) A calibration run was performed using the dilutions of the porcine primary calibrator material dilutions as described in step b) above with the albumin assay reagents and method described in Example 7.

e) A measurement run of the dilutions of the secondary calibrator material according to Example 8c) above was performed using albumin assay according to Example 7 with the porcine primary calibrator material obtained according to step b) above, and the results were interpolated on the calibration curve obtained in the calibration run according to step d) above, and the resulting values of the different dilutions of the secondary calibrator material was noted.

Figure 9:
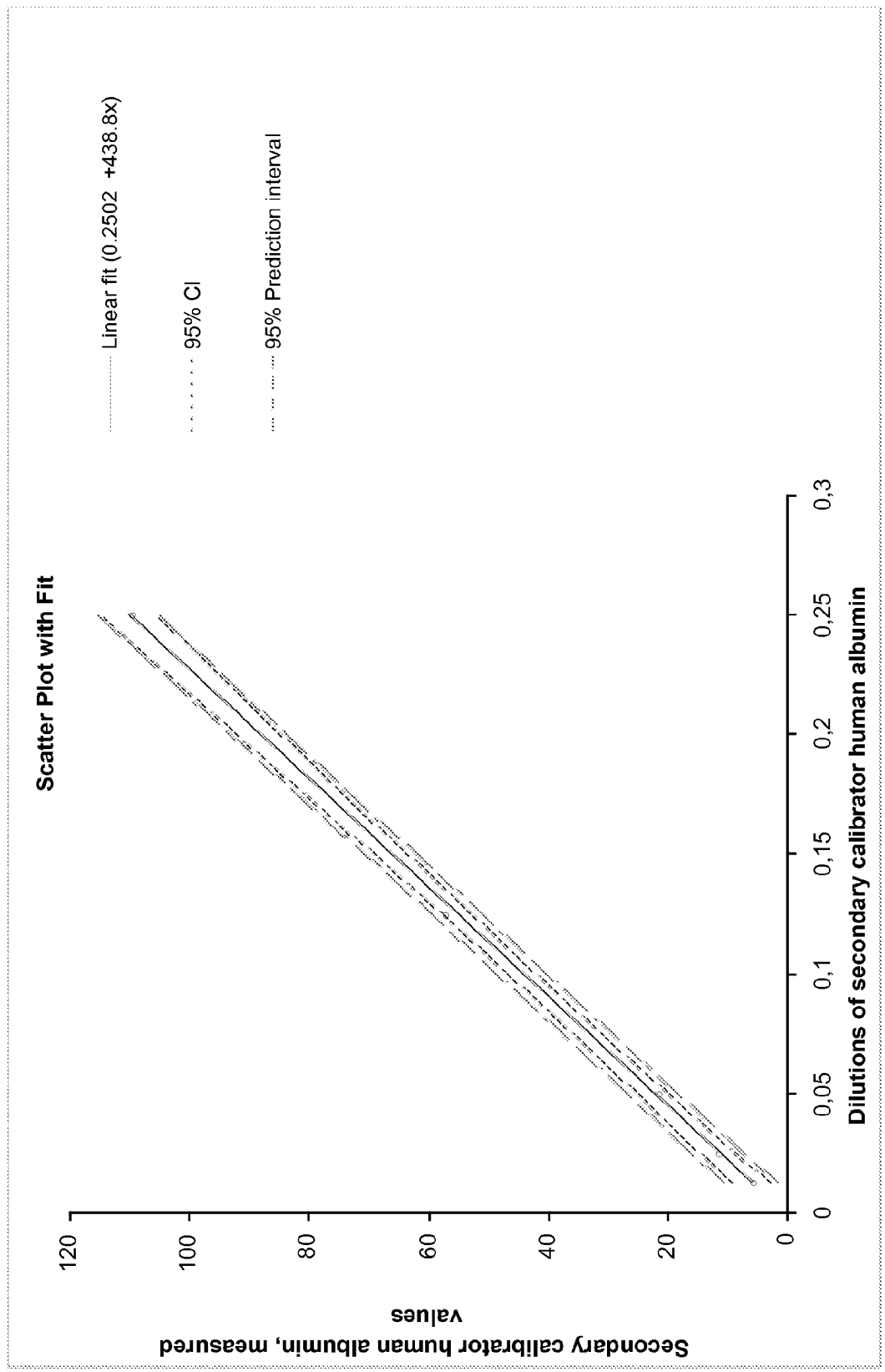

| Primary calibrator Sigma Porcine albumin (mg/l) | Second calibrator Human albumin (mg/l) measured | Secondary Calibrator dilution factor |
|---|---|---|
| 100 | 109.3 | 0.25 |
| 50 | 56.8 | 0.125 |
| 20 | 21.2 | 0.050 |
| 10 | 11.3 | 0.025 |
| 5 | 5.6 | 0.0125 | f) The resulting concentration value points of the different dilution of the secondary calibrator material was plotted against the dilution factor, a best fit correlation curve (using least square value fit) was drawn through the resulting points (see FIG. 9).

The concentration of the undiluted secondary calibrator material could be calculated from the curve and could be assigned to be 439 mg/l in its undiluted form, with a 95% confidence interval of 419 and 458 mg/l This calibration value for porcine albumin was assigned to the secondary calibrator material from Example 8c, although it comprises no porcine albumin

Example 12

A Porcine Urine Albumin Assay without Presence of Porcine Albumin in the Calibrators Using a Secondary Calibrator Comprising Human Albumin (without Presence of Porcine Albumin in the Secondary Calibrator)

A porcine urine albumin assay was made using the assay reagents and methods identical to Example 7, but with the use of the secondary porcine albumin calibrator described in Example 11 above (with a calibrator value obtained in Example 11f) In this way, it was possible to produce an avian antibody based porcine urine albumin assay using antibodies raised against human albumin and with a calibrator based on human albumin, but with porcine albumin values assigned, without presence of porcine albumin in the secondary calibrator.

Example 13

Assay Reagents and Method, and Secondary Calibrators for Assaying Transferrin in Serum and Plasma Samples, and Especially Diluted Serum and Plasma Samples from Different Mammalian Samples Affinity purified chicken anti-human transferrin antibodies prod no. A118Tr were delivered from Norwegian Antibodies AS, Norway.

Immunoparticles and assay reagents were made according to Example 1 and 7. The primary calibrator ERM-DA470 referred to above, which comprises 2.36 gram of human transferrin per litre, was used as primary calibrator for human transferrin.

Secondary transferrin calibrator material was made corresponding to Example 2 above.

The said secondary transferrin calibrator material was assigned value for bovine serum transferrin using purified bovine transferrin delivered from Millipore, US, code no. 82-057-2, comprising 2000 mg/l, using the protocol corresponding to Example 3 above.

The said secondary transferrin calibrator was assigned a value for mouse transferrin using a primary mouse transferrin calibrator delivered from Alpha Diagnostics, Texas, US, product no. 6393, comprising 200 mg transferrin per litre.

An assay method for bovine transferrin and mouse transferrin in different dilutions using the secondary transferrin calibrator comprising human transferrin was made corresponding to Example 4 above.

Methods and reagents for mammalian antigenic analyte assays and secondary calibrators, provided by the present invention using avian antibodies raised against mammalian non-human antigens are other embodiments of the present invention. The assays method and reagents, and calibrators materials for antigen analyte assays of different mammalian species described above, are based on avian antibodies having been raised against mammalian antigens. The basis for the present invention is, however, the surprising discovery that assays method and reagents, and calibrators materials can be used for assay of antigens from different mammalian species, as long as avian antibodies are being used. Therefore, corresponding examples and methods can be made using antigens from other mammalian species than the human species, to raise avian anti-mammalian antibodies. It can therefore be concluded, that antigens from very many, probably most, and maybe all mammalian species can be used to make assays method and reagents, and secondary calibrators materials for antigen analyte assays of different mammalian species, based on avian antibodies towards mammalian antigens. Values for the secondary calibrators can be validated for different mammalian species as described above.

Sets of calibrators can be made: Since many clinical chemistry instrument platforms do an automatic dilution of the calibrator solution to provide a calibration (a calibration curve) over a wide concentration range. Other clinical chemistry platforms use pre-diluted sets of calibrators. All calibrators described above can be provided in the form of ready-made dilutions in serum (or CRP-free serum) or aqueous solution, with or with out salt and/or buffer substances or in other media, well known to the skilled man of the art.

The prior art references as cited herein are incorporated by reference.

The invention claimed is:

1. An immunological assay method for assessing a first analyte in a target sample obtained from a first mammalian species, which method comprises:
   a) obtaining a first analytical signal for said first analyte by contacting said first analyte with an antibody or an antigen binding fragment thereof;
   b) assessing said first analyte by correlating said first analytical signal for said first analyte with a second analytical signal obtained for a second analyte of a second mammalian species different from the first, said second analyte signal having been obtained by contacting said second analyte with said antibody or antigen binding fragment thereof, wherein said first and second analytes are immunologically related;
   wherein:
      said first and second analytes are recognized by said antibody or antigen binding fragment thereof, wherein said antibody or antigen binding fragment thereof is generated in a non-mammalian species in response to the second analyte as antigen; and
   c) calibrating said assay by correlating said second analytical signal obtained for said second analyte of said second mammalian species with said first analytical signal obtained for said first analyte by assigning an analytical value derived from a calibration curve for said second analyte to said first analytical signal of said first analyte.

2. The assay method of claim 1, wherein said first analytical signal and said second analytical signal are obtained by analytical methods that are the same.

3. The assay method of claim 1, wherein at least one of said first and second mammalian species is a non-human mammalian species.

4. The assay method of claim 1, wherein said first and second analytes are functionally and antigenically related.

5. The assay method of claim 1, wherein said first and second analytes are substantially functionally identical and antigenically related.

6. The assay method of claim 1, wherein said first and second mammalian species are different mammalian species and are selected from the group consisting of goat, sheep, rabbit, rat, murine, human, canine, equine, cattle, porcine and feline species.

7. The assay method of claim 1, wherein said non-mammalian species is avian.

8. The assay method of claim 1, which is a particle-based immunological method.

9. The assay method of claim 8, which is a turbidimetric or nephelometric method.

10. The assay method of claim 9, wherein said method further comprises coating nanoparticles with said antibody or antigen binding fragment thereof, thereby forming a nanoparticle-antibody conjugate, wherein the nanoparticles are suitable for turbidimetric or nephelometric measurement.

11. The assay method of claim 10, wherein the antibody or antigen binding fragment thereof comprises polyclonal avian antibodies or antigen binding fragments thereof that are reactive with said first and second analytes.

12. The assay method of claim 1, wherein said target sample is a sample of bodily fluid.

13. The assay method of claim 1, wherein the first analyte is a biological marker associated with a dysfunction, disease or clinical condition of said first mammalian species.

14. The assay method of claim 13, wherein said marker is selected from the group consisting of macromolecules, proteins, glycoproteins, proteoglycanes, nucleic acids and fragments thereof.

15. The assay method of claim 14, wherein said marker is selected from the group consisting of CRPs, transferrins, albumins, serum amyloid protein A, calprotectin, haptoglobin, choriongonadotropins, thyroid stimulating hormone, ferritin, immunoglobulins, insulin, and prostate specific antigen.

16. The assay method of claim 1, wherein a multiplicity of first analytes from a multiplicity of first mammalian species is assessed by correlating a multiplicity of first analytical signals for said multiplicity of first analytes with said second analytical signal obtained for said second reference analyte of said second mammalian species different from said multiplicity of first mammalian species.

17. The assay method of claim 1, wherein said assigned analytical value is further corrected by means of a calibration value.

18. The assay method of claim 1, wherein said first analyte is a first antigenic substance and said second analyte is a second antigenic substance, the assay method further comprising applying a calibrator composition of assays of the first antigenic substance in the target sample, said calibrator composition comprising the second antigenic substance wholly or partially derived from the second mammalian species and assigned with a calibration value valid for said target sample, and wherein said calibrator composition is assigned with calibration values valid for more than one first mammalian species for which the first antigenic substance is to be assessed.

19. The assay method of claim 18, wherein said calibrator is for calibration of CRP assays.

20. The assay method of claim 1, wherein the calibration value is obtained by a method comprising the steps of:
   a) generating a calibration curve with a) primary calibrator material of the first analyte by plotting analytical signals versus related dilutions of said first analyte;
   b) obtaining corresponding analytical signals for different dilutions of the second analyte, whereby steps a) and b) may be performed in any order, and
   c) deriving from said calibration curve of step a) a first analyte related parameter and assigning it to the corresponding analytical signal of the second analyte.

21. The assay method of claim 20, further comprising plotting to assigned first analyte related parameters versus the corresponding dilutions of said first analyte, extrapolating versus dilution factor one and obtaining a calibration value specific for the first analyte.

* * * * *